(12) United States Patent
Acharya et al.

(10) Patent No.: US 10,918,280 B2
(45) Date of Patent: Feb. 16, 2021

(54) NON-INVASIVE BIO-FLUID DETECTOR AND PORTABLE SENSOR-TRANSMITTER-RECEIVER SYSTEM

(71) Applicant: THE JOHNS HOPKINS UNIVERSITY, Baltimore, MD (US)

(72) Inventors: Soumyadipta Acharya, Ellicott City, MD (US); Ashley Polhemus, Meford Lakes, NJ (US); Kevin Colbert, Baltimore, MD (US); Vaishakhi Mayya, Pennington, NJ (US); Aaron Enten, Baltimore, MD (US); Joshua Budman, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 444 days.

(21) Appl. No.: 15/566,754

(22) PCT Filed: Apr. 15, 2016

(86) PCT No.: PCT/US2016/027677
§ 371 (c)(1),
(2) Date: Oct. 16, 2017

(87) PCT Pub. No.: WO2016/168543
PCT Pub. Date: Oct. 20, 2016

(65) Prior Publication Data
US 2018/0116515 A1 May 3, 2018

Related U.S. Application Data

(60) Provisional application No. 62/147,772, filed on Apr. 15, 2015.

(51) Int. Cl.
*A61B 5/1455* (2006.01)
*A61B 5/00* (2006.01)
*G16H 40/63* (2018.01)
*G01N 9/24* (2006.01)
*G01N 21/00* (2006.01)
*G01N 33/72* (2006.01)

*H04B 10/50* (2013.01)
(Continued)

(52) U.S. Cl.
CPC .......... *A61B 5/0022* (2013.01); *A61B 5/1455* (2013.01); *A61B 5/14535* (2013.01);
(Continued)

(58) Field of Classification Search
CPC ... A61B 5/0022; A61B 5/0205; A61B 5/1455; A61B 5/14551; A61B 5/14552;
(Continued)

(56) References Cited

U.S. PATENT DOCUMENTS 8,380,272 B2 * 2/2013 Barrett ............... A61B 5/14553
600/310
8,958,859 B2 * 2/2015 Petersen ............ A61B 5/6826
600/323

(Continued)

FOREIGN PATENT DOCUMENTS

| RU | 2294223 C2 | 2/2007 |
| WO | 2013149001 A1 | 10/2013 |
| WO | 2013149011 | 10/2013 |

OTHER PUBLICATIONS

International Search Report and Written Opinion for the Application No. PCT/US2016/027677, dated Jul. 28, 2016, 11 pages.

*Primary Examiner* — Chu Chuan Liu
(74) *Attorney, Agent, or Firm* — Harrity & Harrity, LLP

(57) ABSTRACT

The present invention is directed to a bio-fluid detector such as a hemoglobin detector having the capability of receiving, storing and transmitting health information utilizing a portable transmitter and receiver including electronic PDAs such as cell phones. Further, the present invention utilizes a non-invasive hemoglobin detector that is connected to a portable transmitter-receiver such as PDAs including, but not limited to, cell phones.

20 Claims, 21 Drawing Sheets

(51) Int. Cl.
*A61B 5/145* (2006.01)
*G01S 19/00* (2010.01)
*G06F 19/00* (2018.01)
*G01N 33/49* (2006.01)
*G16H 50/30* (2018.01)

(52) U.S. Cl.
CPC .......... *A61B 5/6826* (2013.01); *A61B 5/6838* (2013.01); *A61B 5/7264* (2013.01); *A61B 5/743* (2013.01); *G01N 9/24* (2013.01); *G01N 21/00* (2013.01); *G01N 33/4925* (2013.01); *G01N 33/72* (2013.01); *G01S 19/00* (2013.01); *G06F 19/3418* (2013.01); *G16H 40/63* (2018.01); *H04B 10/50* (2013.01); *A61B 2560/0214* (2013.01); *G01N 2333/805* (2013.01); *G16H 50/30* (2018.01)

(58) Field of Classification Search
CPC ..... A61B 5/6826; A61B 5/7264; A61B 5/743; A61B 5/6838; A61B 5/14535
See application file for complete search history.

(56) References Cited

U.S. PATENT DOCUMENTS

| | | | |
|---|---|---|---|
| 2002/0038078 A1* | 3/2002 | Ito | A61B 5/14551 600/309 |
| 2004/0030229 A1* | 2/2004 | Norris | A61B 5/14552 600/323 |
| 2004/0102687 A1 | 5/2004 | Brashears et al. | |
| 2007/0197885 A1* | 8/2007 | Mah | A61B 5/1455 600/310 |
| 2008/0001735 A1 | 3/2008 | Tran | |
| 2008/0081974 A1* | 4/2008 | Pav | G16H 50/20 600/336 |
| 2008/0242958 A1* | 10/2008 | Al-Ali | A61B 5/02427 600/323 |
| 2010/0240973 A1* | 9/2010 | Presura | A61B 5/14551 600/335 |
| 2012/0016219 A1 | 1/2012 | Fujii | |
| 2012/0108928 A1* | 5/2012 | Tverskoy | A61B 5/0059 600/324 |
| 2015/0066378 A1 | 3/2015 | Robison et al. | |

\* cited by examiner

PHONE PROCESSES SIGNAL AND PRESENTS USER INTERFACE

PORTABLE, HANDHELD DESIGN ALLOWS FOR REMOTE USE

DATA UPLOADED TO CLOUD FOR SURVEILLANCE

DATA COLLECTION WITH FINGER CLIP

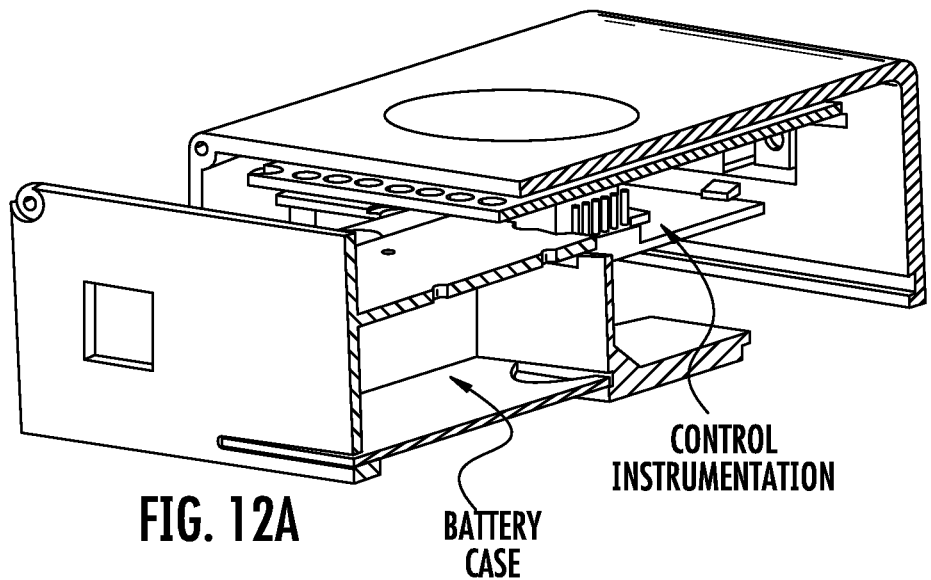
FIG. 12A  BATTERY CASE  CONTROL INSTRUMENTATION
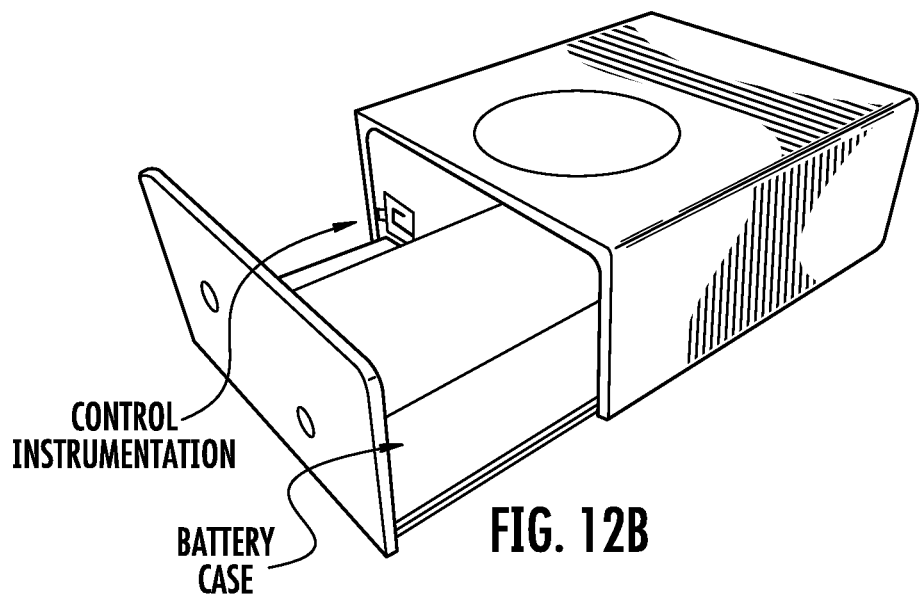
CONTROL INSTRUMENTATION  BATTERY CASE  FIG. 12B

NON-INVASIVE BIO-FLUID DETECTOR AND PORTABLE SENSOR-TRANSMITTER-RECEIVER SYSTEM

CROSS-REFERENCE TO RELATED APPLICATIONS

This application is a 35 U.S.C. § 371 U.S. national entry of International Application PCT/US2016/027677, having an international filing date of Apr. 15, 2016, which claims the benefit of U.S. Provisional Application No. 62/147,772, filed Apr. 15, 2015, the content of each of the aforementioned applications is herein incorporated by reference in their entirety.

GOVERNMENT SUPPORT

The present invention was made with government support under AID-OAA-F-13-00006 awarded by USAID. The government has certain rights in the present invention.

FIELD OF THE INVENTION

The present invention relates generally to medical screening. More particularly the present invention relates to a device and method for determining hemoglobin levels in blood.

BACKGROUND OF THE INVENTION

Anemia is a condition characterized by a low amount of red blood cells or hemoglobin content in blood, resulting in an impaired ability of the blood to transport oxygen. Moderate to severe anemia is particularly dangerous during pregnancy for both the mother and the baby. 100,000 maternal deaths and 600,000 neonatal deaths worldwide are attributable to anemia each year. The prevalence of anemia in the developing world is staggering, with estimates by the WHO reaching up to 50% among pregnant women and 65% among children. Of these total cases, there is a subgroup of severely anemic pregnant women who are at risk for life-threatening complications during gestation and especially during birth; moderate-severe anemia is associated with higher risk of perinatal complications such as post-partum hemorrhage, a major cause of maternal death. In total, anemia is estimated to be a direct or indirect cause of 26% of maternal deaths in India. In addition to this toll, millions of infants worldwide are affected by maternal anemia through morbidities ranging from low birth weight, failed lactation, neonatal sepsis, to impaired cognitive development.

Over the past few decades, a number of developing nations, particularly India, have conducted programs of state sponsored iron and nutritional supplementation. The efficacy of these programs has not been well documented and the benefits they provide are often the subject of debate. The reason for this dearth of clear benefits is unclear. One possible factor is a lack of compliance among those at risk. Most cannot be screened for anemia and are thus unaware of the severity of their condition and the need for supplementation. There is also a lack of anemia education and the marketing of an effective public health message involving iron supplementation.

One crucial step towards improving compliance and efficacy of anti-anemia programs is the implementation of a system to track the progress of a given intervention by the large-scale collection of hemoglobin levels of pregnant women. There is thus a need for a device that is able to be used widely and cheaply to screen for anemia, with the aim of reinforcing existing programs in India and other nations by identifying those at the highest risk, especially those with moderate-severe anemia in late gestation, in order to bring them "out of the cold" and into existing healthcare structures. Moreover, if able to track patient data geographically and over time, such a device would facilitate macro-scale public health policy by enabling the targeting of health care initiatives to areas in need and by providing feedback on interventions. Finally, such a system would increase the accountability of the programs, allowing for more efficient application of limited resources.

The current standard of care for anemia detection includes the clinical pallor test and the WHO color scale. Blood based assays are only performed at equipped laboratories and hospitals, well out of reach of the average citizen of a developing nation. As a result, few are screened at all, and those who are, are screened by methods that are not sufficiently objective. The noninvasive pallor test is based on the color of the conjunctiva tissue of the eye, relying on the judgment and experience of the healthcare worker, which is often limited, in order to determine whether or not the patient has anemia.

The WHO color scale is an invasive test that requires a drop of blood be placed on a special piece of paper and dried. The color is then compared to a reference swatch. This test is also quite variable depending on the environmental conditions (lighting, humidity) in which the test is performed, and the results are again subject to variable judgment and experience. Moreover, the test is invasive and introduces discomfort and the risk of infection.

Pulse oximeters are well known in the art. The theory behind hemoglobin detection is based on the absorbance of light by hemoglobin in the blood. Pulse-oximetry based hemoglobin meters use 7+ wavelengths to detect concentrations of all species of hemoglobin, including methemoblogin and carboxyhemoglobin, to company stated accuracies of ±1 g/dL. While these types of devices are highly accurate, they are not adaptable to lay users and are often cost prohibitive and overly complex for implementation in developing nations as a screening tool. There are known scientific attempts made at pulse-oximetry based hemoglobin detection, but these attempts achieved better accuracy than required for the purposes of use in developing nations and at far greater cost and complexity.

Frequency modulation based communication between a sensor and a smart phone are known in the art. The Project Hijack device, designed by students at the University of Michigan, is aimed at the iPhone™ and iPad™, and uses a frequency based analog to digital conversion method to communicate with the phone. The phone is then able to decode this frequency based digital signal. The disadvantage of this is the complexity of circuitry in their design and of the frequency modulation scheme.

It would therefore be advantageous to provide a device that reduces the variability of the standard of care in an easy to use, cost-effective manner.

SUMMARY

According to a first aspect of the present invention a system for determining hemoglobin level in a subject's blood includes a mobile communication device and a sensor system. The sensor system includes a light emitting diode (LED) configured to transmit light through tissue of the subject at four wavelengths. A photosensor is configured to receive and measure light transmitted through the tissue of the subject by the LED. Additionally, a communications board is configured to trigger the LED to transmit light, configured to receive information related to the light received by the photosensor, and further configured to communicate with the mobile communication device.

In accordance with an aspect of the present invention, the system also includes an LED driver and a timer coupled to the LED driver. A power source is included for providing power to the sensor system and can take the form of a battery or the mobile communication device. The communication board further comprises an amplifier, and the amplifier can take the form of an AM or BFSK device. The mobile communication device can take the form of a cellular telephone that has a headset-in jack and a headset-out jack. The LED can take the form of two LEDs. A wavelength of light emitted by a first LED of the two LEDs can be 660 nm and a wavelength of light emitted by a second LED of the two LEDs can be 810 nm.

In accordance with another aspect of the present invention, a sensor system for detecting hemoglobin in a subject's blood includes a finger clip configured to be disposed on a fingertip of the subject. The system also includes a light emitting diode (LED) configured to transmit light through tissue of the subject and disposed on a first surface of the finger clip adjacent to the fingertip of the subject. Additionally, the system includes a photosensor configured to receive and measure light transmitted through the tissue of the subject by the LED and disposed on a second surface of the finger clip opposite the first surface of the finger clip. A communications board is configured to trigger the LED to transmit light and configured to receive information related to the light received by the photosensor.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 11A illustrates a smartphone. FIG. 11B illustrates data collection, displaying the plethysmogram. FIG. 11C illustrates patient data collection and user interface. FIG. 11D illustrates patient information located on a computer application based map, and FIG. 11E illustrates a heat map showing severe and moderate cases of anemia from a field study in Eastern India.

FIG. 12A illustrates a sectional view of the housing showing placement of the battery and the control instrumentation and FIG. 12B illustrates a top-perspective view of the housing.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a bio-fluid detector such as a hemoglobin detector having the capability of receiving, storing and transmitting health information utilizing a portable transmitter and receiver including electronic PDAs, such as cell phones. Further, the present invention utilizes a non-invasive hemoglobin detector that is connected to a portable transmitter-receiver such as PDAs including, but not limited to, cell phones.

Figure 8A:
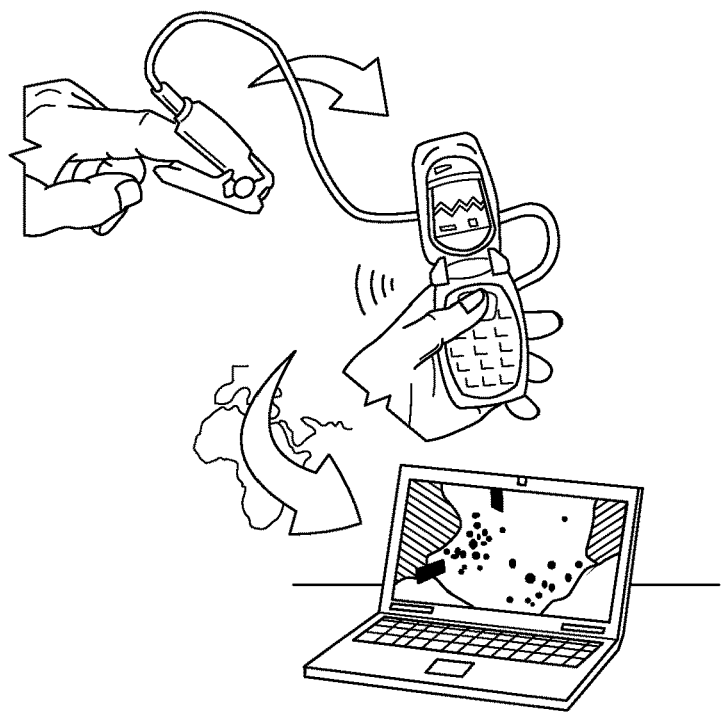
FIG. 8A illustrates a schematic diagram of the system according to the present invention.
Figure 8B:
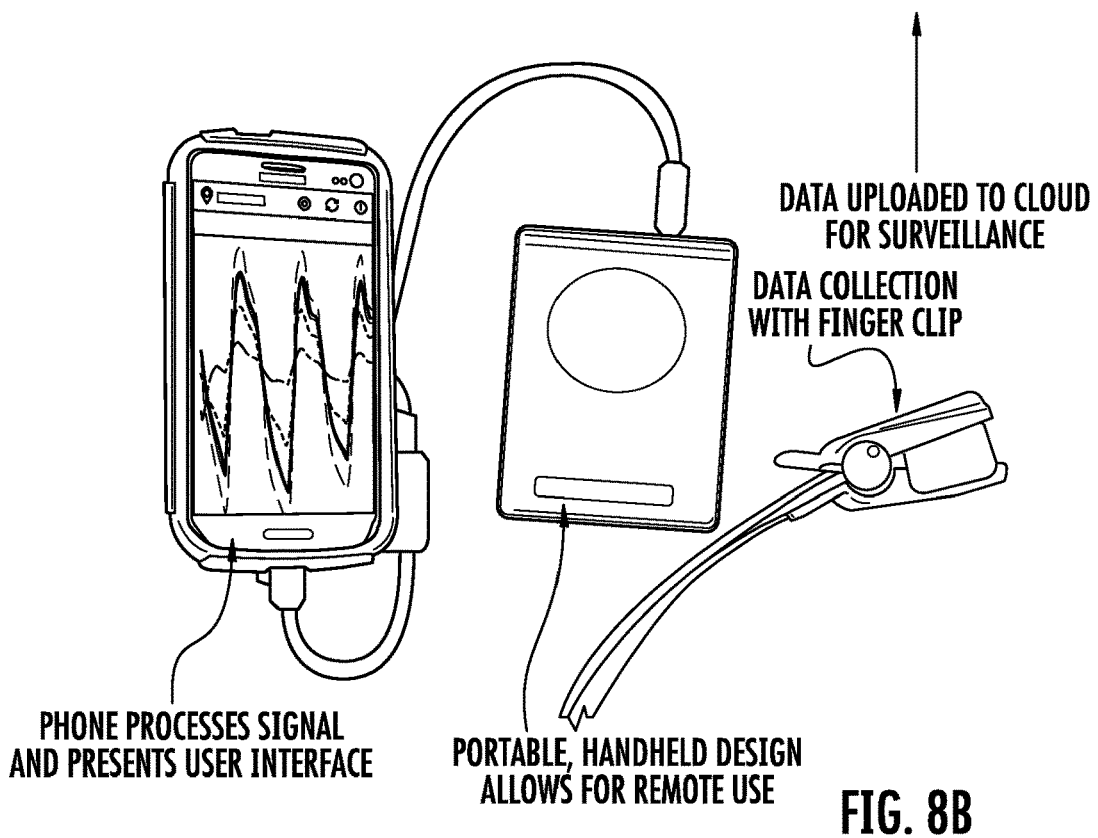
FIG. 8B illustrates a preferred embodiment of a device according to the present invention.

The present invention is further directed to a noninvasive telemedicine-enabled hemoglobinometer that has the potential to shift the paradigm for anemia screening. The cost and functionality of the device facilitate screening by community health workers (CHWs) in periphery areas, extending quality care to mothers living far from traditional health care services. The device collects physiologic data with a finger clip and converts optical signals into a hemoglobin assessment using a categorical classification algorithm based on non-linear machine learning. The results are displayed on the screen of the cellphone, in a color-coded, pictographic representation, to allow semi-literate community health workers to appropriately counsel pregnant women on the next steps. The system leverages the global ubiquity of mobile phones to report the findings to a central server, as illustrated in FIG. 8A and FIG. 8B. FIG. 8A illustrates a schematic diagram of the system according to the present invention, and FIG. 8B illustrates a preferred embodiment of a device according to the present invention. The associated online platform enables programmatic quality assurance, individualized patient follow-up, large-scale anemia surveillance, and effective governmental resource allocation.

The basic principle of optical hemoglobin detection is based upon spectroscopy, and the Beer-Lambert law:

$$I = I_{0,\lambda} e^{-\Sigma_i \varepsilon_{i,\lambda} \cdot \delta \cdot c_i}, \quad (1)$$

$\varepsilon$=extinction coefficient of material i at wavelength $\lambda$,
$\delta$=path length of light,
$c_i$=concentration of material i,
$I_0$=incident light intensity,
$I$=transmitted light intensity According to equation (1), under ideal conditions the intensity of transmitted light through a solution can be related to its composition. Under laboratory conditions, hemolyzed blood is often accordingly analyzed at several wavelengths to determine precise concentrations of different types of hemoglobin; this is sometimes used to determine levels of carboxyhemoglobin in blood during postmortem investigation of fire or carbon monoxide related deaths.

Photoplethysmography is used to acquire absorbance data from blood without the need for a blood sample. Light at specific wavelengths, in this case at the isosbestic wavelength for deoxy and oxyhemoglobin, 810 nm, is shone through tissue, often the finger or the earlobe, and the transmitted light is captured. During transmission, a portion of the light passes through the artery within the finger and is absorbed by hemoglobin within the blood. This blood absorption component varies with time according to the changing diameter of the artery during systole and diastole. Detectable in the intensity of transmitted light, therefore, is a pulsatile component whose magnitude is directly related to the magnitude of absorption of arterial blood.

One problem that arises in passing light through tissue is unpredictable scattering and absorption of light due to the heterogeneity of the tissue and the light path; this can be compensated by a ratiometric approach:

$$O.D_{810} \approx \frac{\frac{AC_{810}}{DC_{810}}}{\frac{AC_{ref}}{DC_{ref}}} \quad (2)$$

O.D=optical density,
AC=the pulsatile component of the signal, in this case the peak to peak magnitude,
DC=the non-varying component of the signal Within the DC component of the denominator and numerator are components attributable to the thickness, opaqueness and geometry of the tissue, independent of the specific wavelength of light used; therefore, these components cancel out in (2), and what is left is a reliable measure of a ratio of AC's. Conveniently, if the denominator contains a reference wavelength independent of Hb, then the ratio becomes robust to fluctuations in blood volume and the reliability of the measure is increased.

The measure of interest is simply the optical density or the absorption due to blood in the artery at 810 nm. The magnitude of this density or absorption is intrinsically correlated to hemoglobin concentration, as hemoglobin is the major absorptive component of blood in the NIR range. The use of 810 nm light, for which the extinction coefficients of oxy- and deoxy-hemoglobin are equal, ensures a relationship unaffected by changing oxygenation levels between the total concentration of deoxy/oxyhemoglobin, together constituting 90-95% of normal blood hemoglobin content, and the absorption of 810 nm by blood. Thus, estimation of this absorption leads directly to an estimate of hemoglobin content.

One final caveat is that the scattering of light by disc-shaped whole blood cells introduces a small degree of non-linearity into the system. The Twersky equation (3) is an accepted characterization of this non-linear relationship. Importantly, in physical ranges, it has been shown that the relationship between hematocrit and light absorption is nearly linear; consequently, it can be argued that the relationship between hemoglobin concentration and absorption can be approximated as nearly linear in the physical range, especially if extreme accuracy is not a requirement, as in the present invention.

Figure 1:
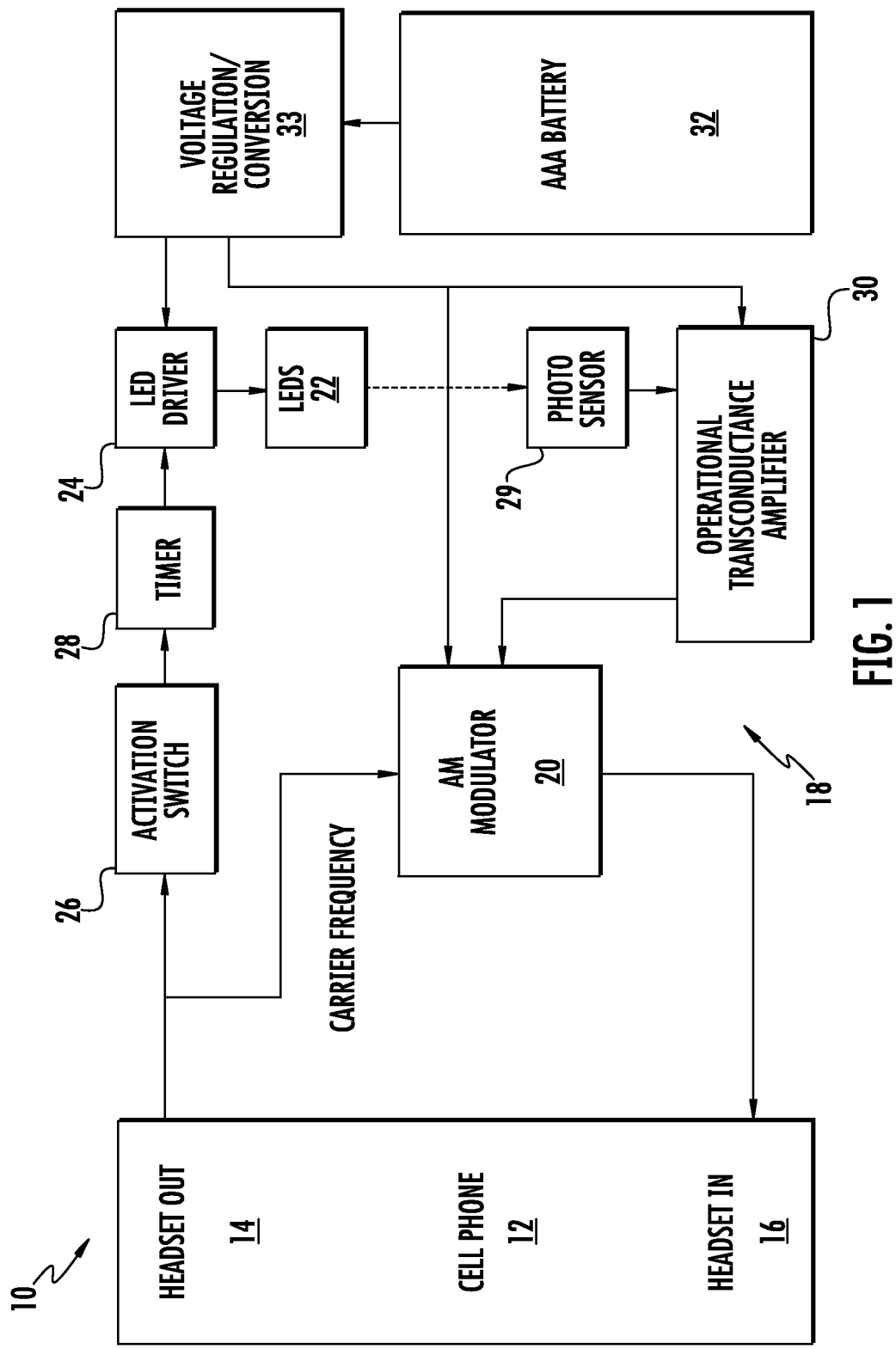
FIG. 1 illustrates a schematic diagram of a device for measuring hemoglobin in the blood, according to an embodiment of the present invention.

Twersky's equation:

$$O.D = \log_{10}\left(\frac{I_0}{I}\right) = \varepsilon \delta c - \log_{10}[10^{-a\delta h(1-h)} + q(1 - 10^{-a\delta h(1-h)})] \quad (3)$$

where $\varepsilon$, $\delta$, c are the same as before,
a=constant dependent on size of RBCS, refractive index, and wavelength,
h=fractional hematocrit,
q=constant dependent on RBC size, refractive index, wavelength, and the aperture angle of the photodetector FIG. 1 illustrates a schematic diagram of a device for measuring hemoglobin in the blood, according to an embodiment of the present invention. As illustrated in FIG. 1, the device 10 includes a cellphone 12 having a headset-out sound transmitter 14 and a headset-in port 16. A sensor system 18 taking the form of a finger clip, not illustrated in the schematic diagram, is coupled to the cellphone 12 via the headset-in port 16. The sensor system 18 includes a circuit board (not shown), referred to as a communication board, including a communication device 20 to transmit communication from the sensor system 18 to the cellphone 12. The sensor system 18 also includes an LED 22 and an LED driver 24. The LED driver 24 is coupled to an activation switch 26 and also a timer 28 in order to activate the LED for a hemoglobin reading. The LED 22 is used to transmit light to a photosensor 29 to determine the amount of the light transmitted from the LED through the tissue of the subject to the photosensor 29. The photosensor 29 transmits the light information to an operational transconductance amplifier 30 that is configured to transmit information about the light information to the cellphone 12. External battery power 32 can be used to power the system, rather than the more limited power that can be harnessed from the headset jack of the cellphone itself. A voltage regulation/conversion device 33, therefore, may also be needed. A completely cell-phone powered device also is possible with the utilization of low-power LEDs and circuitry.

The sensor system 18 can include a low-power, ultra-cheap sensor, in order to keep costs down for use in developing nations. The sensor system 18 plugs into and communicates with low-end cellphones 12 via the headset-in port 16, a nearly universal feature on cell phones. Computation can be provided by an applet on the cellphone itself, and power either by a small battery or the cellphone itself. Computation can also be done on MATLAB on a laptop, using the computer's microphone and headphone jacks as stand-ins for a cellphone headset jack.

Figure 2:
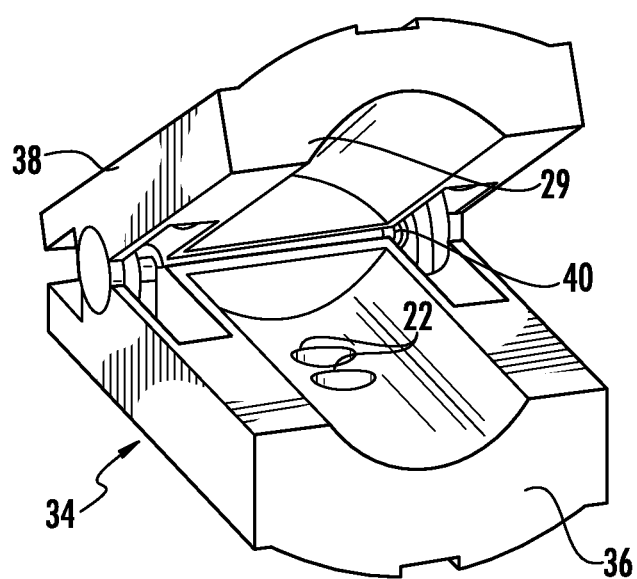
FIGS. 2 and 3 illustrate perspective views of the finger clip, according to an embodiment of the present invention.
Figure 3:
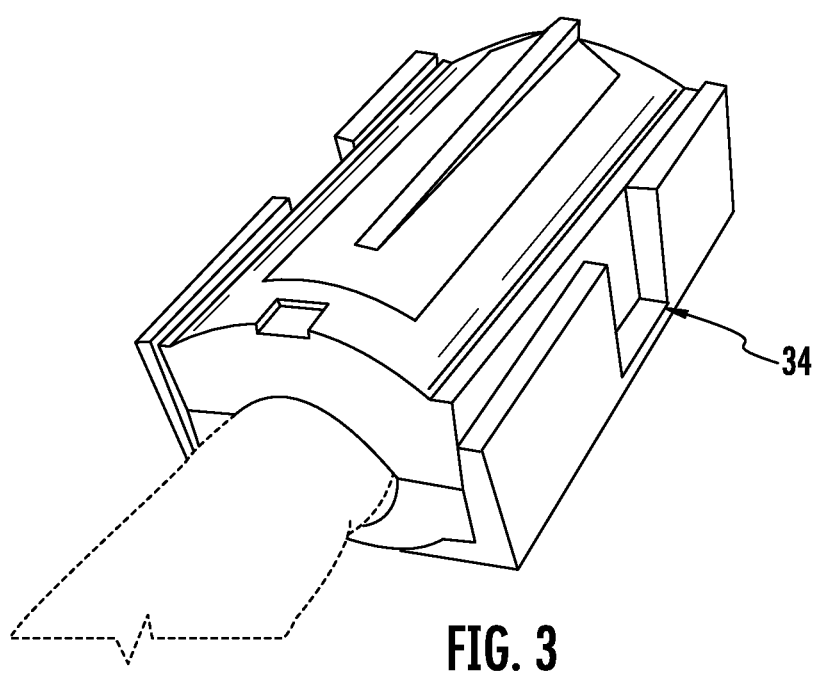

As discussed above with respect to FIG. 1, the sensor system 18 includes the circuit board and a finger clip containing LED's 22 and the photosensor 29 or photodiode. FIGS. 2 and 3 illustrate perspective views of the finger clip, according to an embodiment of the present invention. The finger clip 34 includes a bottom piece 36 to hold the photosensor 29, a top piece 38 containing the LED's 22, and a torsion spring 40. The finger clip can be formed from plastic, rubber, or any other suitable material known to one of skill in the art. The torsion spring 40 is configured to hold both the bottom piece 36 and the top piece 38 together, as well as keeping the clip clamped shut to reduce interference from external light. The entire finger clip 34 is preferably covered in matte black paint in order to reduce noise from the scattering and reflecting light inside the sensor.

The sensor system 18 includes LED's 22, at wavelengths selected from a group of 522, 569, 570, 590, 660, 810, 940, 1050, and 1070 nm. The LEDs are configured to allow the light generated to shine through the finger, either index or middle, and be collected by a photosensor 29. In a preferred embodiment LEDs with four distinct wavelengths of 569, 660, 810, and 940 nm are used. However, any number of LEDs producing any number of wavelengths of light could also be used, as is known to or conceivable by one of skill in the art. The group of wavelengths used in the preferred embodiment are based on test results and the absorption spectra of oxyhemoglobin, deoxyhemoglobin, water, and fatty tissue. The LEDs are centered over the fingernail when the system is placed on a patient's finger. A silicon-based photodiode is located in line with the LEDs on the underside of the finger. When each LED is activated, monochromatic light passes through the finger. Some of that light is scattered, some is absorbed by blood constituents, and the rest is transmitted to the photodiode, which converts light energy to current. The diode produces a plethysmogram-shaped waveform, which is transmitted to the system's control instrumentation. In a preferred embodiment of the invention only one wavelength is applied at any given time and the LEDs are pulsed successively by a microcontroller in functional control of the LEDs.

Figure 13:
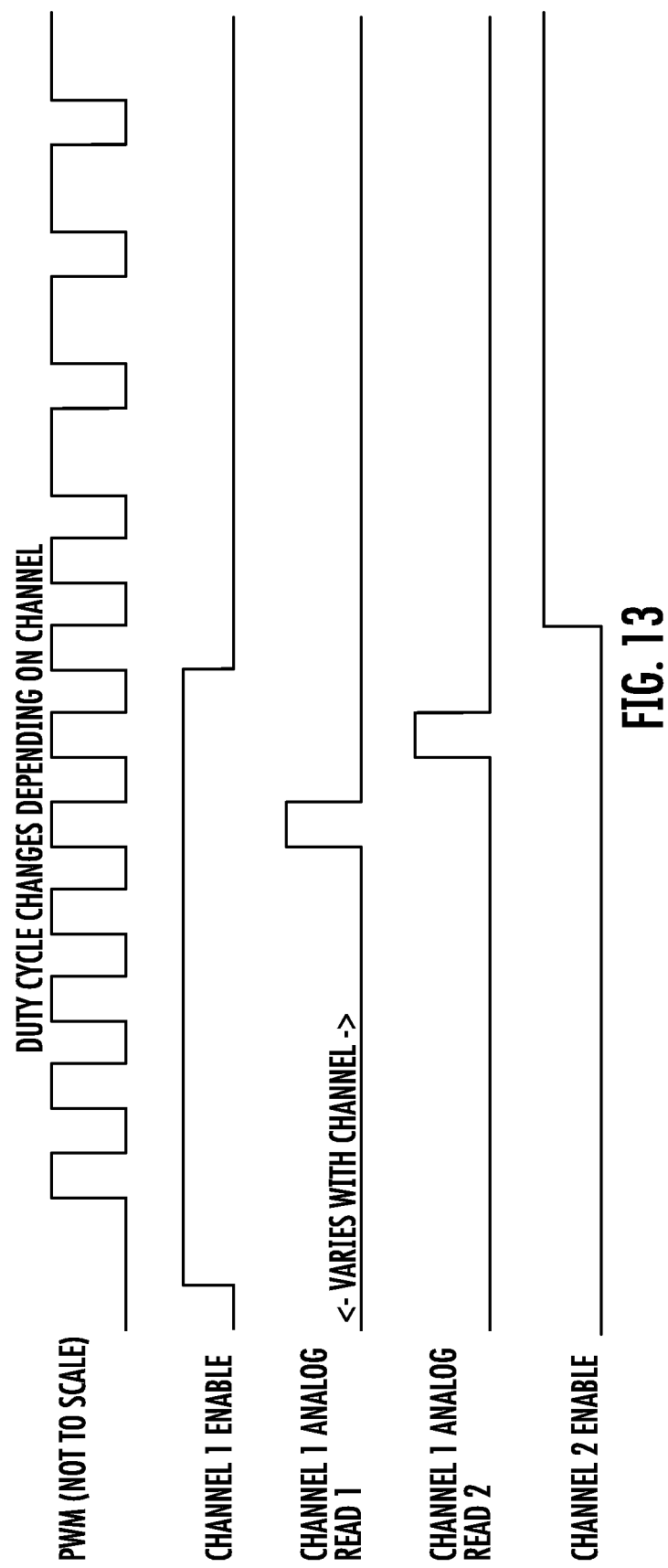
FIG. 13 illustrates graphical views of details for the four channel drive algorithm.

The device cycles through the wavelengths over a predetermined period of time. For example, the wavelengths may be cycled every 20 ms. The computing device associated with the system knows which wavelength is being applied and therefore takes this information into account in the calculations. The control instrumentation, which is run by a PIC microcontroller, in a preferred embodiment, cycles through each channel, one after the other at 40 Hz (that is, 40 Hz on each channel). When a channel is enabled, the output of the transimpedance amplifier is directed to the channel's filtering circuitry by an analog switch and the other channels are disabled. After several hundred microseconds, two 12-bit analog reads are performed on each channel. One of these is the raw plethysmogram after the transimpedance amplifier; the other is the filtered and further-amplified plethysmogram, which is centered on a virtual ground of 2.5 volts. The current channel is subsequently disabled, the next channel's PWM value is written to the PWM output, and the process repeats. FIG. 13 illustrates graphical views of details for the four channel drive algorithm.

Figure 14:
FIG. 14 illustrates a chart showing data encoding details for this communication protocol.

At the end of a complete cycle (through all four channels), the data is encoded and dumped to the mobile phone. Each piece of data is sent with three bytes: a code word to signify a valid data point; a second byte containing the channel ID, the type of data point, and the upper four bits of the data point; and a third byte, which is the low byte of the data point. FIG. 14 illustrates a chart showing data encoding details for this communication protocol.

Figure 9:
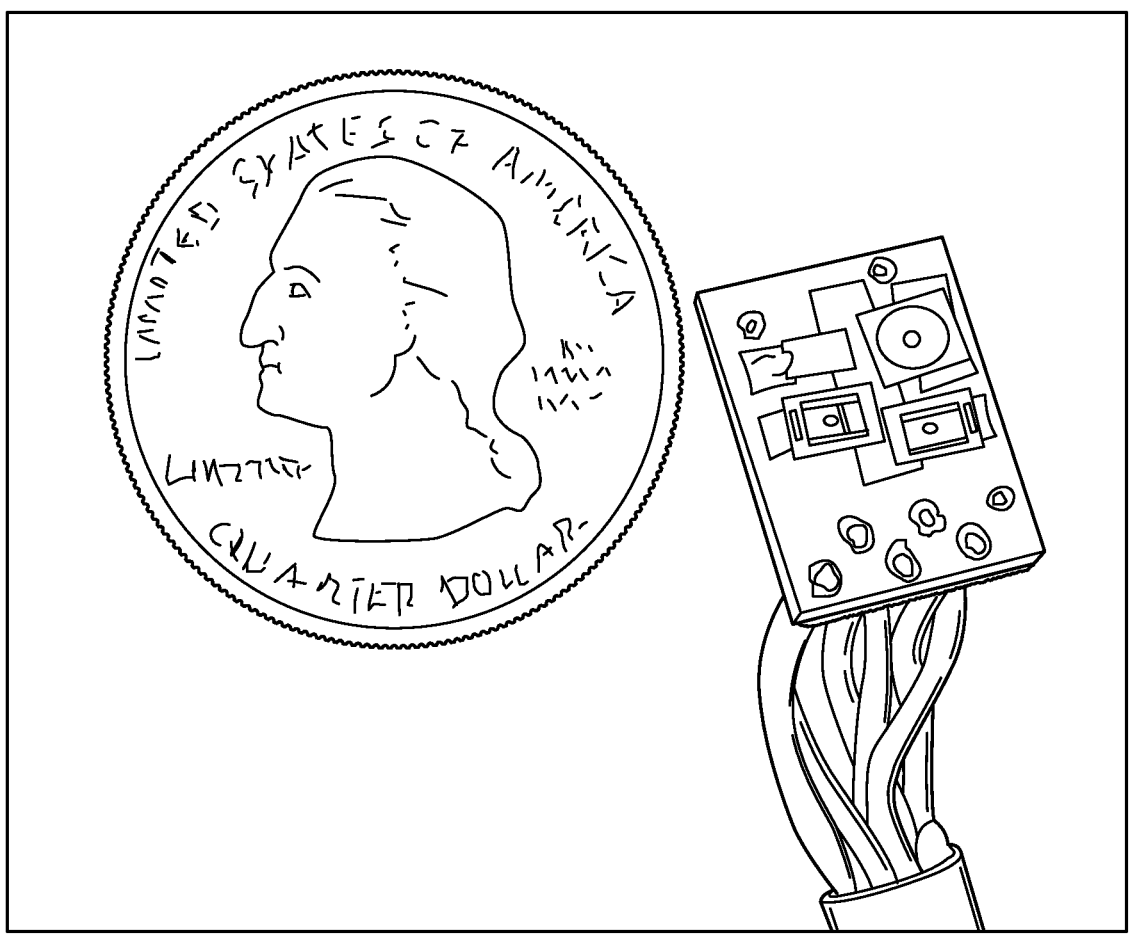
FIG. 9 illustrates an LED layout for a finger clip according to a device of the present invention.

Light at lower wavelengths (in this case, 569 nm), cannot pass through the finger reliably unless high intensity light is used. While no marketed LED fit the needs of this prototype, it was discovered that two medium-intensity 569 nm LEDs could produce a reliable signal when activated in parallel. Therefore, in a preferred embodiment five total LEDs (having four unique wavelengths) were used in a preferred embodiment of the invention. The resulting footprint of the point sources in these LEDs was 3.0 mm×3.5 mm, well under the 4 mm×6 mm constraint derived from a measurement of fingernail area of a small woman, as illustrated in FIG. 9. FIG. 9 illustrates an LED layout for a finger clip according to a device of the present invention. The LEDs are installed on a 3D printed baseboard or any other suitable board configured to mount and contain the circuit board holding the LEDs and photodiodes. The baseboard is secured to the housing of the sensor, significantly decreasing motion artifact and ensuring that LED placement relative to the finger is consistent.

Figure 10:
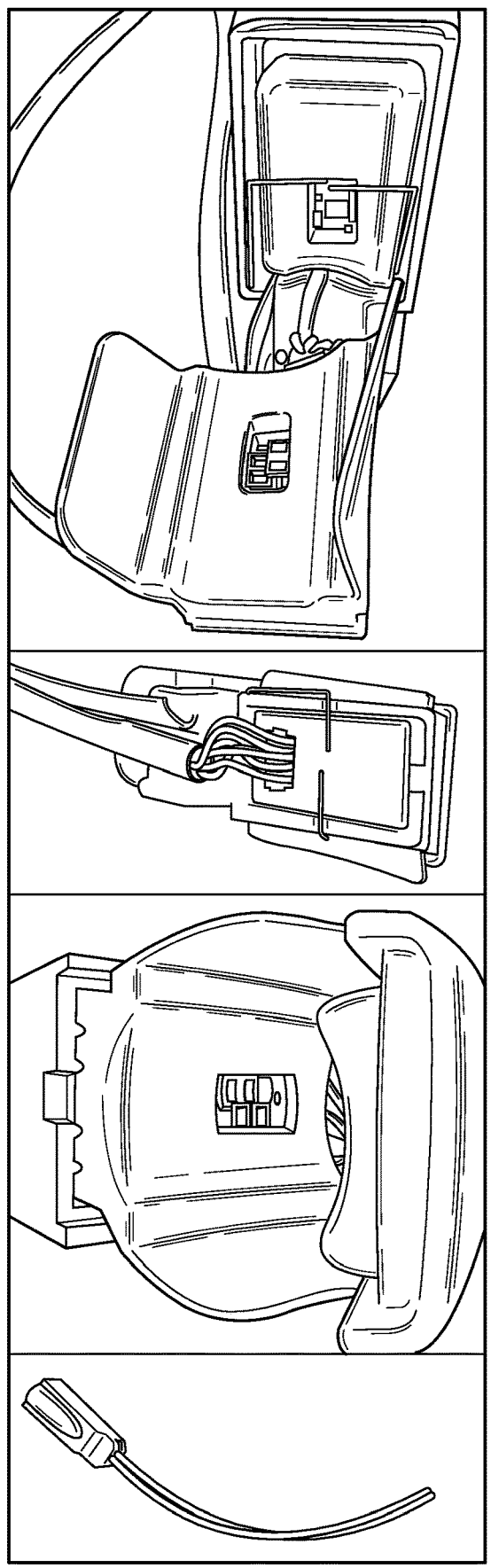
FIG. 10 illustrates a finger clip design according to an embodiment of the present invention.

The probes include base plates as measures for strain relief, as illustrated in FIG. 10. FIG. 10 illustrates a finger clip design according to an embodiment of the present invention. Channels driving LEDs are shielded and insulated separately from those carrying the waveform generated by the photodiode in an attempt to exclude noise from the drive circuit. Probes connect through a standard 9-pin D-Sub connector. Sensor variability testing is ongoing with identical protocols to assess the inter- and intra-probe variability, the effect of battery level on acquired signals, and the effects of finger placement in the device.

Based on the Beer-Lambert law, the intensity of the light absorbed by the photosensors is related to the absorption of the substances within the medium through which the beam passes. Photoplethysmography is a method that uses this absorbance data to extract information specifically on the contents of the blood. Because arterial blood absorption increases and decreases, when there is a in blood volume during systole and diastole, within the resulting signal is a small pulsatile wave, called the plethysmograph. The properties of this pulsing signal, including amplitude and time variation, can be assumed to be related to changes in the arterial blood component only.

Figure 7:
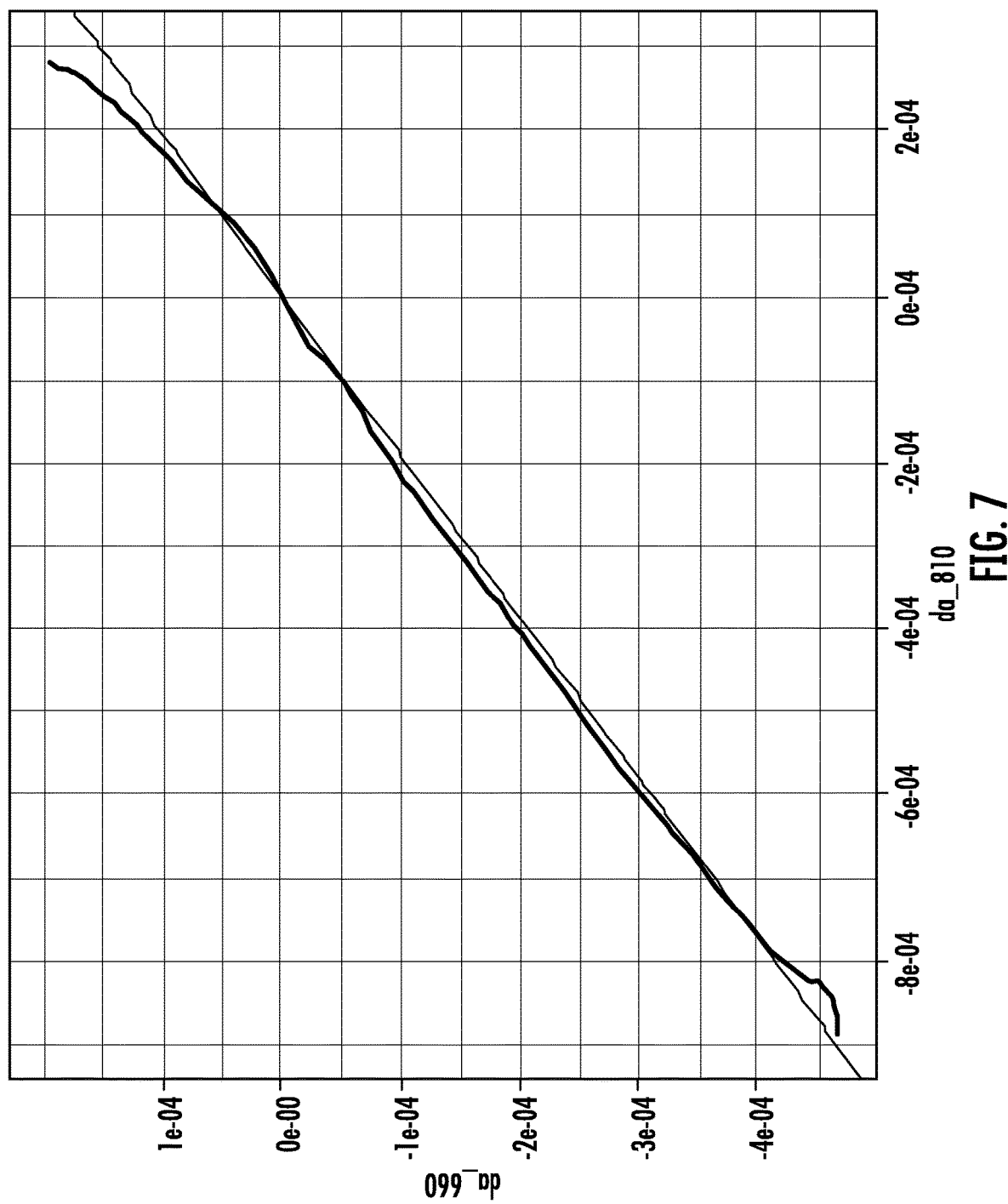
FIG. 7 illustrates a graphical view of the slope-correlation method, used according to an embodiment of the present invention.

When using light shone through tissue, there will be unpredictable scattering and reflection of light. In order to reduce the effect of the unpredictable scattering and reflection of light caused by components of tissue such as geometry and opacity, a ratiometric approach is used where the parametric slope of the time-derivatives of waveforms at two wavelengths is calculated. This method is roughly equivalent to the usual method of calculating a ratio of ratios of AC, or varying component, over DC, non-varying component, at two wavelengths used in pulse oximetry, but is expected to be more reliable under varying conditions, due to its use of a larger amount of the available information of a waveform, and its reliance on the ratios of time variance, rather than pure amplitude, of the waveforms. FIG. 7 illustrates a graphical view of the slope-correlation method, used according to an embodiment of the present invention. The slope of the linear interpolant of $dA_{\lambda,1}$ versus $dA_{\lambda,2}$ is the parametric slope or slope correlation method, represented by the equations reproduced below.

Represents the constant components of tissue $$DC_a = \boxed{f(r_a, r_f, \lambda)} DC, \quad DC = DC_a + DC_b \quad (4)$$

$$\Delta OD_{tot} = AC/DC_a = [1/f(r_a, R_f, \lambda)]AC/DC \equiv (1/f)R$$

$$R_{ij} \equiv \frac{R_i}{R_j} = \frac{AC_i/DC_i}{AC_j/DC_j} = \frac{f(r_a, r_f, \lambda_i)\Delta OD_{tot,i}}{f(r_a, r_f, \lambda_j)\Delta QD_{tot,j}} \approx \frac{\Delta OD_{tot,i}}{\Delta OD_{tot,j}},$$

$$f(r_a, r_f, \lambda_i) \approx f(r_a, r_j, \lambda_j)$$

$$dA_\lambda = \frac{I_i - I_{i-1}}{(I_i + I_{i-1})/2}, \quad (5)$$

The AC component contains information on the arterial blood while the DC component contains the absorption from the tissue shape and path. In order to obtain data for both wavelengths of light, the two lights need to be on at different times to obtain data for each specific wavelength. In the present invention, the pulse is recorded from one wavelength for 10 seconds, and then the LED's are switched manually and data is obtained from the second. The switching process can also be automated, through a frequency dependent switch controlled by tones played by the cellphone. Moreover, the LED's may eventually be pulsed at high rates using 555 timers, as in pulse oximetry; this has the advantage of reducing optical noise, and allows simultaneous, rather than sequential, collection of waveforms at 2 wavelengths, increasing the reliability of measures. Finally, because the present invention will measure a single value of Hb, rather than continuous values, as in pulse oximetry or commercial plethysmography based Hb-meters, from data that is averaged over time, the method can be expected to be more noise resistant. Further noise resistance can be conferred by the use of noise-identifying and rejecting methods (autocorrelation) for rejecting of aberrant pulses caused by motion artifacts or other sources of noise; this is not implemented in the current design.

Rejection of bad samples was done by judgment, based on the waveforms during initial testing. There is also the issue of the differing average transmission of light from person to person caused by a variety of factors; someone might possibly saturate the photodiode, or oppositely not provide a strong enough signal. This problem is corrected using an auto gain control component, which tunes the voltage driving the LEDs, if the output average voltage is too high or too low, such that the DC voltage it levels off around a 2-2.5V region (out of a maximum operation range of 0-3.3V or 5V) where a pulse is visible. The gain control tuning takes from approximately 2-8 seconds to stabilize. The device can be tuned manually using variable resistance trimpots.

Figure 4:
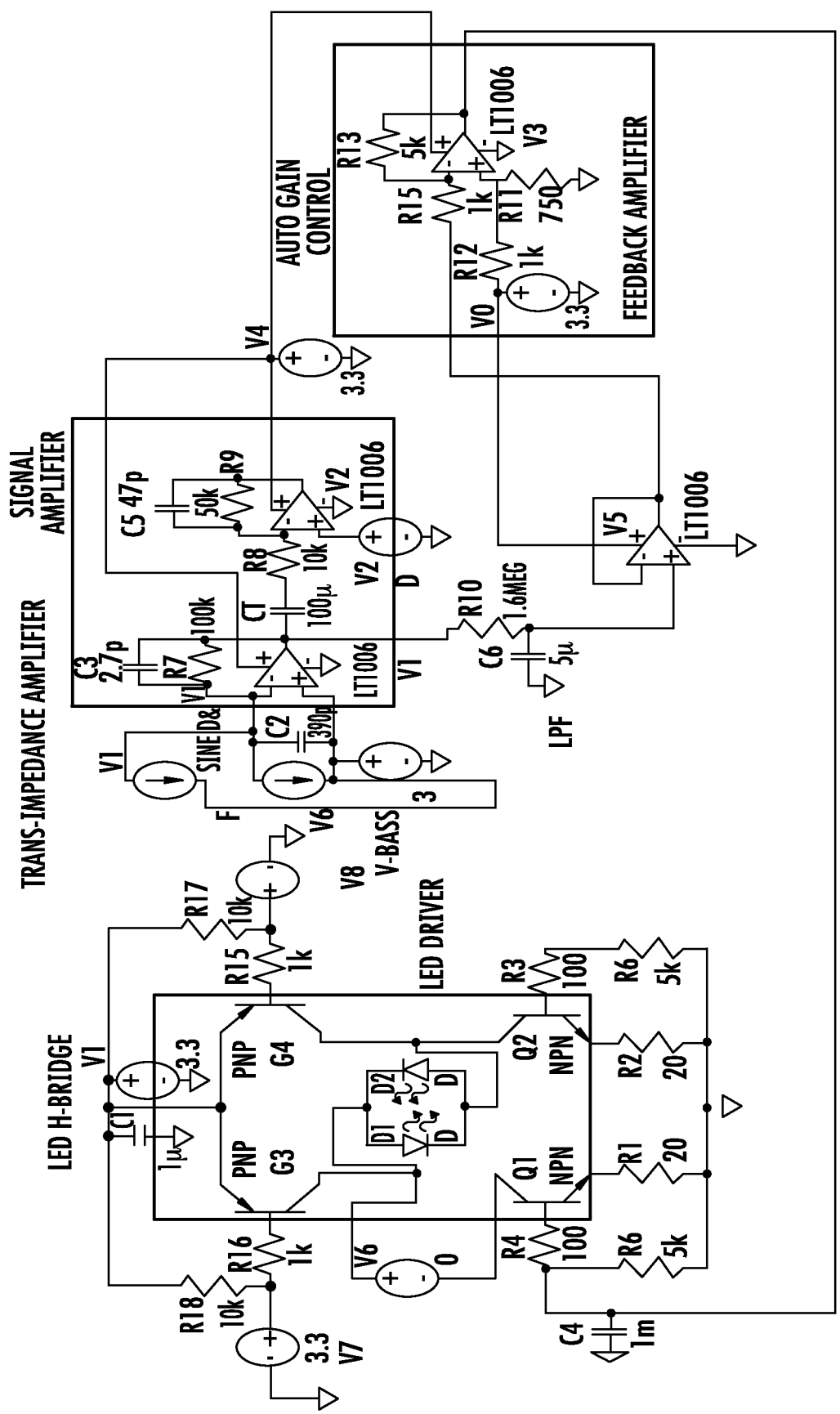
FIG. 4 illustrates a circuit diagram of a main sensor board, according to an embodiment of the present invention.

Another important aspect of the present invention is the communication board. FIG. 4 illustrates a circuit diagram of a main sensor board, according to an embodiment of the present invention. Preferably, the communication board can take the form of a separate, small, self-contained device that plugs into the cellphone via the headset jack and acts as communicator between various sensors—including the photosensor—and the cellphone. These sensors could also take the form of interchangeable peripherals. The versatility of such a device would be invaluable, allowing data of a large range of types to be collected and relayed remotely via cellphone; for example, soil and water pH, EKG readings, air pollution, among others. Two possible methods of communication can be used to implement the present invention. However, any other method of communication known to or conceivable by one of skill in the art could also be used. One such method is amplitude modulation (AM) and another such method is binary frequency shift keying (BFSK).

Figure 5:
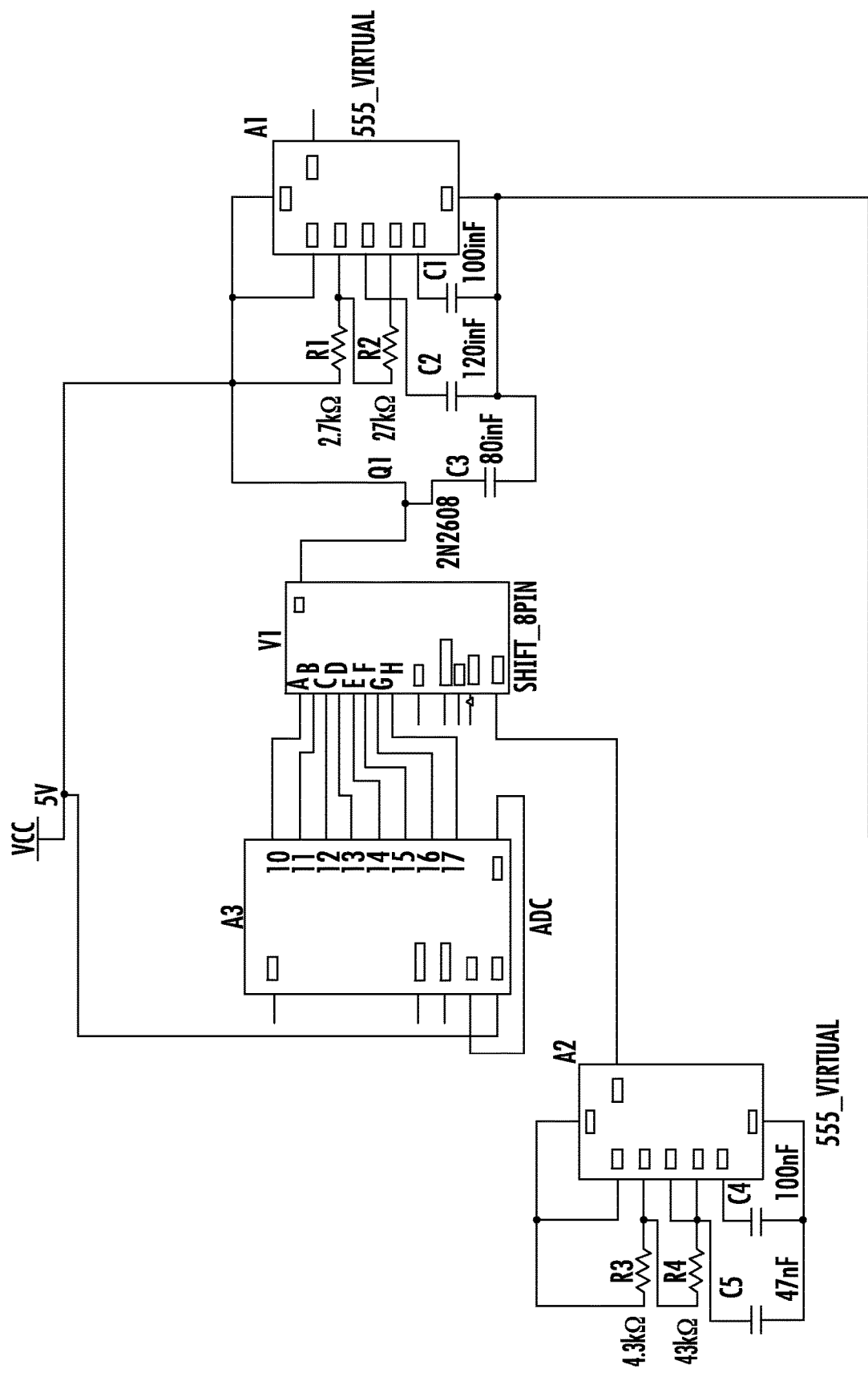
FIG. 5 illustrates an exemplary circuit diagram of a BFSK communication board according to an embodiment of the present invention.

FIG. 5 illustrates an exemplary circuit diagram of a BFSK communication board according to an embodiment of the present invention. BFSK is discussed herein as the preferable device for communication due to its versatility and noise resistance, and ability to transmit messages unchanged due to its digital nature. Amplitude modulation is simpler, but also potentially as difficult or more difficult to demodulate, and is subject to information loss and a narrow range of operation. The key constraint for any communication method is the fact that the cell phone audio jack is AC coupled, and therefore any signal passed to it must be of a frequency in the accepted range, approximately 300 Hz-3 kHz. Briefly, AM multiplies a low frequency signal with a carrier wave (sinusoidal) of high frequency. The resulting signal can be passed to the audio jack and demodulated within the phone by an envelope-detection algorithm.

The control instrumentation comprises the hardware components and software algorithms developed to collect and process the data from the finger clip. It is the component that controls the LEDs and receives electrical signals from the photodiode. The electrical signal is filtered, amplified, and processed to acquire a usable signal. The pulsatile plethysmographic (PPG) signals obtained from the finger are very weak and noisy, constituting just 2%-3% of the entire signal. As a result, extensive post processing filtering and amplification are required to remove electrical noise and amplify the PPG signal. The battery and the control instrumentation are housed in a custom designed housing illustrated in FIG. 12A and FIG. 12B. FIG. 12A illustrates a sectional view of the housing showing placement of the battery and the control instrumentation and FIG. 12B illustrates a top-perspective view of the housing. The housing is connected between the computing device or smartphone and the finger clip. The battery in the housing provides power for the finger clip electronic components as well as the control instrumentation. The control instrumentation is in wired or wireless communication with the computing device, smartphone, server or other device. The control instrumentation can also be networked to other devices, an associated server or other computing related system.

The instrumentation utilizes an onboard microcontroller in order to generate, acquire, and transmit both raw plethysmograms and processed data to a cell phone. The microcontroller is programmed with a non-transitory computer readable medium that simultaneously 1) modulates a series of switches that alternate power distribution to each of the four transmitting channels, and 2) reads signal acquisition channels. A pulse width modulator is used to supply self-adjusting current levels to the sensor's light emitting diodes. The transmitted signal received from the photodiode is amplified through a custom transimpedance amplifier. The microcontroller's analog to digital converter reads and stores the voltage output at a rate of 40 Hz for each of the four channels. The signals are then passed through a series of filters: a notch filter to exclude electrical noise at 50 Hz, as well as active and passive high and low pass filters that result in an effective bandwidth of 0.8-5.0 Hz.

The photoplethysmogram corresponding to each individual LED can be isolated and the maximum and minimum voltages of the pulsatile component measured. This is used to obtain a ratio of ratios, called R, which is calculated with two wavelengths and can be correlated to hemoglobin concentration. More complex analysis can yield R values for three or more wavelengths, and additional wavelengths can strengthen the correlation between an R-value and a resultant hemoglobin value. Where $V_{AC}$ and $V_{DC}$ are the values for LEDs 1 and 2 of the alternating and DC baseline, respectively.

$$R = \frac{\ln(VAC1/VDC1)}{\ln(VAC2/VDC2)} \quad (6)$$

One issue is that compression is done automatically by the phone when accessing the headset-in port. It may therefore be difficult to obtain a full spectrum waveform in pure form; low frequencies—i.e. the signal of interest—may be filtered out automatically by hardware within the phone in its attempt to isolate vocal harmonic frequencies for use in transmitting sparse voice information. On the other hand, if these specific frequencies are known, then a method using only one or two of them is at a significant advantage. BFSK is a simple digital communication method dating to the 1950's, when it was used by Bell 202 telephone modems; it simply represents binary 1 and 0 as two well-separated frequencies.

An efficient algorithm for calculating the power of presence of a specified frequency, Goertzel's algorithm, can then be used to decode the signal representing the bit-stream. By avoiding the calculation of fast Fourier transforms over all frequencies, the algorithm makes implementation of tone detection possible in a low computation setting—such as a low end cellphone. Conversion of a voltage signal to a digital signal is accomplished by an analog-digital converter (ADC). This digital signal is then encoded in BFSK by a specific circuit. The present invention is used in conjunction with a cell phone software application preferably coded in Java. Any other coding language or software application known to or conceivable by one of skill in the art could also be used. A pictorial display of anemia level can be provided for the healthcare worker via the GUI, and a numerical value can be logged and accessed. Further, the numerical hemoglobin value can be sent via SMS to a central server. A MATLAB script on a personal computing, tablet, or other computing can be used to acquire live data, display it, and analyze it either in real time or at a later point in time.

A carrier frequency for amplitude modulation (AM) is provided by a tone played at a specific frequency by the phone, and outputted via the headset-out channel. If a cellphone has stereo capability, two separate channels are available. If two channels are available, one may be used to either harvest power via a rectification and step-up circuit, or to provide frequency based commands to the system, for example to a frequency dependent LED driver, wherein different frequencies cause a different LED to be turned on, similar to what occurs in a light organ. If a cellphone has only mono capability, this channel can be dedicated to the carrier frequency, while signals are being transmitted. However, interceding data acquisition periods—during which a single LED will be on for a specified time and data recorded, this channel may be used temporarily to command the circuit to "switch" wavelengths, using a frequency dependent switch. This avoids the need for any kind of microcontroller on the external sensor board, maximizing what is done by the cell phone and minimizing the complexity and cost of the overall device.

The cellphone will thus be able to obtain the signals from the sensor by modulating the plethysmograph signal onto the carrier, and inputting the resulting waveform into the headset-in input of the headset-jack. By AM, a signal can be represented by manipulating the amplitude of the carrier wave.

Given a carrier wave represented by the function:

$$c(t) = A_c \cos(w_c t + \varnothing_c) \quad (7)$$

Where $A_c$ is the amplitude, $\varnothing_c$ is the initial phase, and the frequency (Hz) of the wave can be expressed as we, and the signal to be expressed by the carrier wave is given by the function:

$$S(t) = A_S \sin(w_S t + \varnothing_S), \quad (8)$$

Where $A_S$ is the amplitude, $\varnothing_s$ is the initial phase, and the frequency (Hz) of the wave can be expressed as $$\frac{w_c}{2\pi},$$

and the signal to be expressed by the carrier wave is given by the function:

$$S(t) = A_S \sin(w_S t + \varnothing_S), \quad (9)$$

where $A_S$ is the amplitude, $\varnothing_S$ is the initial phase, and the frequency (Hz) of the wave can be expressed as $$\frac{w_S}{2\pi},$$

and the frequency of the carrier wave is much greater than the frequency of the signal, or $$\frac{w_c}{2\pi} \gg \frac{w_S}{2\pi},$$

the AM signal can be expressed as the product:

$$S_{modulated}(t) = [1 + S(t)] * c(t) \quad (10)$$

AM is commonly used to transmit radio waves over long distances, and is a less noise-robust but simpler method than frequency modulation (FM). In this device, AM using a carrier wave in the vocal range (1-10 khz) is required for the cellphone's AC-coupled mic input to detect the signal. Once the AM signal has been captured by the cellphone, a computationally inexpensive envelope-detecting method is used to extract the original signal, which involves finding the focal maximums of the AM signal. Given that the pulsatile signal is at a much lower frequency than the carrier, it is possible to retain almost all the information of the original signal.

Figure 6:
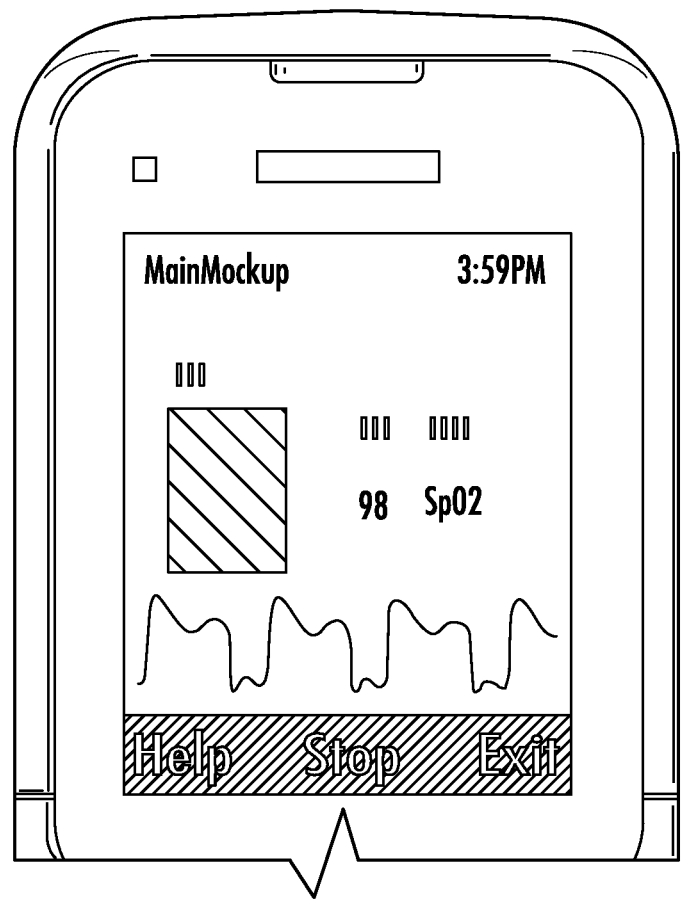
FIG. 6 illustrates an image of a cellphone displaying a signal, according to an embodiment of the present invention.

Thereafter, all calculations are performed by the applet on the cellphone. FIG. 6 illustrates an image of a cellphone displaying a signal, according to an embodiment of the present invention. The estimated hemoglobin concentration is converted into an easily interpreted visual icon on the graphical user interface on the cellphone screen. This icon can consist of a pictorial depiction and/or a color expressing the anemic state of the patient. It is preferable that the data for display is presented in a simple way, so that it can be displayed on the GUIs of a basic phone, and a smartphone need not be used, unless one is available. During the initialization of the device, the screen will display feedback to let the user know if the sensor is correctly connected, and if usable signals are being acquired from the patient. During data acquisition, a real time display of the plethysmograph waveform will be displayed in a portion of the screen, as illustrated in FIG. 6. At the same time, a menu system on the applet will allow the health worker to input the name and other important information. This information will be stored and eventually relayed, together with the hemoglobin reading and anemia status, via SMS to a permanent database. Importantly, this relaying of a message allows the location of the reading to be determined via cell phone tower locations, and documented. All of this information is invaluable to local health departments in public health planning, and tracking of critically anemic pregnant women for follow up care.

In another embodiment of the present invention, a single wavelength of light is used, 810 nm, rather than two. This will allow for an extremely simple sensor board including only of the LED and a light detection circuit, and the AM system.

Another embodiment of the present invention uses three wavelengths of light. Two of the wavelengths are the wavelengths commonly used in pulse oximetry, 660 nm (red) and 930 940 nm (IR), and 810 nm. This will allow the device to be used in addition as a pulse oximeter, and the cellphone applet will contain options to enable pulse oximetry and/or hemoglobin detection.

In another alternative embodiment of the present invention, frequency modulation (FM) is used rather than AM to communicate with the cellphone. In particular, binary frequency-shift-keying (BFSK) is a more noise-resistant, and still relatively simple method of communication using frequency. These frequencies will need to be generated on the sensor, requiring analog to digital conversion and increasing the complexity and cost of the device. However, the digitization of data allows a much greater variety of data to be transmitted, not just voltage. In addition, BFSK is more reliable, and ultimately more sensitive than AM for communicating data to the cellphone. BFSK consists of two tones, each representing a 1 or a 0. Decoding on the cell phone side can be done relatively cheaply, which in turn allows for higher transmission rates.

Data analysis unveiled a non-linear behavior in the physiologic plethysmogram of patients with lower hemoglobin values compared to the behavior of patients with higher hemoglobin values. In order to properly assess the non-linear input-space, the device uses support vector machines (SVM) to analyze the patient data. An SVM is a non-probabilistic binary linear classifier. This allows separation of data into two discrete groups. SVMs were chosen because the classification is better suited against the "curse of dimensionality" allowing it to perform well despite the scarcity of data retrieved from anemic patients. The first SVM was used to classify patients as "anemic" or "healthy" based on whether a value greater than or less than 10.5 g/dL was detected. After this, the patients in the anemic group were isolated and a second WM was used to classify "mild" anemia as patients with hemoglobin values between 9-10.5 g/dL and "moderate to severe" anemia as patients below 9 g/dL. Finally, it is important to note that the output from the SVM is a matrix of constants, allowing all computation to be done on a mobile phone. The classifiers are trained independently and then combined to increase accuracy. This is a committee technique of training the classifiers. As noted above, the trained matrix is on the non-transitory computer readable medium on the patient-side device. The device can be further networked to a server and/or a cloud server to update the matrix. Results from committee calculation of the classifiers are then pushed back to the patient-side device.

The finger clip sensor is connected to a mobile phone with a phone application designed for use with the present invention. After a hemoglobin concentration is determined and reported to the user, the application sends the patient specific data to a secured central server. The geo-tagged data is agglomerated to output a heat map of anemia prevalence to a Google Map in real-time. Eventually, data will be made available securely to nonprofit organizations as well to health ministries in the respective countries.

The device of the present invention is envisioned to classify patients into four anemia classifications (normal, mild, moderate, severe). In this way, the technology is intended to be used as a screening tool in areas without local health facilities. Providing information on the categorical bucket a woman falls within could empower her to make her own decisions regarding the necessity of seeking treatment. Furthermore, this use case provides a method for the government to improve reporting in hard-to-reach areas. The real-time value mapping software would be extremely useful to enable ubiquitous data collection.

The goal of the interface design is to simplify the process of anemia screening for the health care worker. A simple "green, yellow, orange, red" interface will alert the health worker to "none, mild, moderate, and severe" anemia levels. The software will then guide the health care worker towards the appropriate course of action, i.e:
1. None (green): "Maintain diet and iron/folic acid pill regimen. Visit the health care facility on a regular basis."
2. Mild (yellow): "Maintain diet and iron/folic acid pill regimen. Visit the health care facility on a regular basis."
3. Moderate (orange): "If you have stopped your iron/folic acid pill regimen, then resume. Seek an appointment at a health care facility as soon as possible.
4. Severe (red): "Visit a health care facility immediately for appropriate intervention." In this case, the health care worker might even facilitate the patient's immediate visit to a clinic or hospital.

The back-end dashboard tracks severity of anemia on an individual case basis with traceability to GPS co-ordinates, and phone number of originating device. The dashboard has temporal and spatial statistics of anemia severity at a macroscopic (state), mesoscopic (local district) and microscopic (individual patient) level. On the back-end all data is transmitted to a central server (or servers) that store the reading's geolocation, hemoglobin levels, and CHW identifiers, which can then be accessed by any computer with internet access, Different levels of security protocols could be used to maintain patient confidentiality. The server centrally stores the data and generates intuitive flags and heat maps to indicate severe and moderate cases of anemia.

In a preferred embodiment, a custom Android application was developed to serve as a user interface. Any other suitable computer application or platform could also be used, and the invention is not limited to Android, a cellphone, or an "app" format. The user has the ability to input patient name, age, gestational age, and location. The cell phone receives and stores the waveform transmitted by the control instrumentation. The application then identifies segments of the waveform where no movement artifact or other noise obscures the plethysmogram signal, and submits the signal to a classification algorithm. This algorithm determines whether the waveform is consistent with properties of either anemic or non-anemic waveforms, and classifies the patient into "buckets" of severe/moderate anemia, mild anemia, or no anemia. Through a connection to the cloud or through SMS, the hemoglobin assessment and the patient data are sent to a central server and added to a database. This database allows doctors to access patient records and government officers to map the distribution of severe, moderate, mild anemia in a desired area.

Figure 11E:
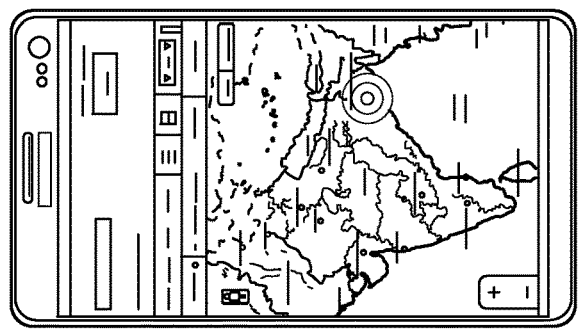
FIGS. 11A-11E illustrate screen shots from application. More particularly.
Figure 11D:
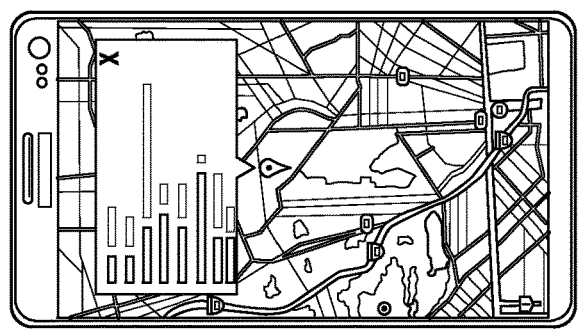
Figure 11C:
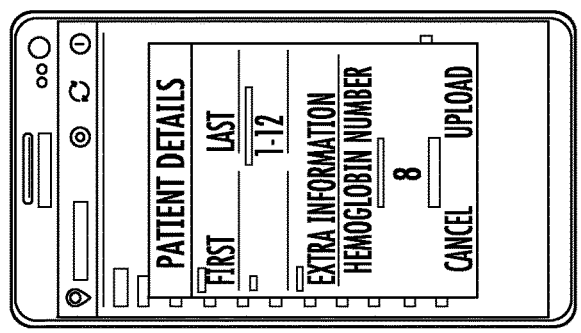
Figure 11B:
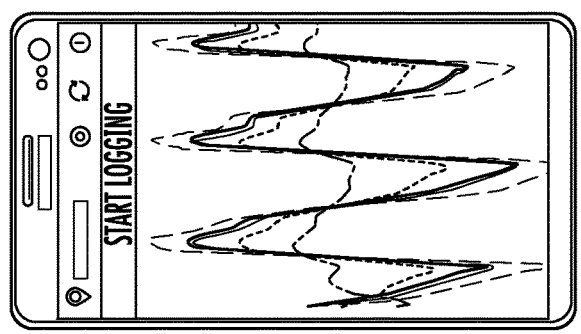
Figure 11A:
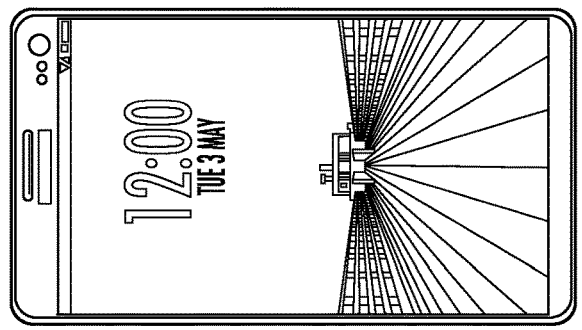

The operating system takes input from the user and the device and updates a map application. FIGS. 11A-11E illustrate screen shots from the computer application of the present invention. More particularly, FIG. 11A illustrates a smartphone. FIG. 11B illustrates data collection, displaying the plethysmogram. FIG. 11C illustrates patient data collection and a user interface. FIG. 11D illustrates patient information located on a computer application based map, and FIG. 11E illustrates an exemplary heat map showing severe and moderate cases of anemia from a field study in Eastern India. The invention could also be implemented using a basic or feature phone, to allow for greater dissemination.

On a macro-scale, a device with geographic and chronologic patient data tracking capabilities will facilitate public health policy development within developing countries. Such a platform will allow Ministries of Health and NGOs to identify regions encumbered with disparate rates of anemia prevalence and provide targeted health care initiatives. In addition, such a system will increase the accountability of healthcare programs, allowing for optimal distribution of limited resources. The cell phone platform of the present invention enables seamless reporting of patient data at the district, state, and national level.

The present invention also has the potential to be expanded to a mHealth data acquisition platform. After validation of the finger clip anemia tool, other low cost sensor based diagnostic/screening tools such as a blood pressure monitor or a 2-lead electrocardiogram can be added to the CHW's arsenal of patient screening tools. Regardless of the sensor, the telemedicine enabled platform has the potential to alter global healthcare.

The control of device parameters (wavelengths used, intensity of light, duration of pulse, algorithm used for classification) may be influenced by individual patient profiles located in the "cloud" or other remote server. When the device accesses the server on the cloud, it may update patient profiles with parameter information. Or, in an effort to protect patient privacy, profile information may only be stored on the cloud, but accessed at the beginning of a test. For instance, 1. a health worker would input patient identifying information into the device,
2. the device would access the patient's personalized profile online in a secure database
3. the device would retrieve patient specific parameters based on previous calibration and stored blood test information
4. the device would use the patient specific parameters to calibrate
5. the health worker would run the test
6. the device would send the test raw data to the online database
7. back-end calculations may be performed in the cloud (online database) to conserve power and memory on the device
8. the device would report the results from the back-end calculations to the health worker/patient where, "device" refers to the sensor, physical control box, and phone or other mobile device.

As the mapping software develops, privacy and confidentiality concerns will be of utmost concern. During the implementation stages, the online platform will be structured with differing levels of access depending on clearance. For instance, tertiary care doctors may only be able to see their respective geographical area, while the Director of the Ministry of Health may have access to country wide statistics. The communication protocols between the phones and server will also need to be encrypted prior to any scaled implementation.

The current design has "hard coded" calibration curves, which are used to estimate hemoglobin ranges. However a non-wired version of this, whereby the development team will be able to remotely access the calibration curve and update it. The devices will periodically pull the new calibration curve from the cloud, instead of having it hard coded. This will allow for more frequent iteration on the entire system of the present invention.

A basic or feature phone implementation also allows for greater dissemination of the system of the present invention. The choice to build a Java app is based on a recent survey from Nepal showing that two-thirds of health care workers have Java based phones. Basic phones do not allow for micro-USB or USB communication so the communication protocol between the sensor and phone is revised. Therefore, the system can also be configured for data transmission over the audio jack of basic phones.

It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, RFID, or any other suitable data transmission means known to or conceivable by one of skill in the art.

Exemplary Implementations

The following examples are included merely as illustration and are not meant to be considered limiting. Any implementation conceivable to one of skill in the art could also be used.

Studies were conducted. Post-study statistical analyses attempted to identify a relationship between the hemoglobin readings from the device of the present invention and the gold standard. The studies were also used to identify potential improvements in the mechanical design of the finger clips, electrical components of the device, and usability of the GUI.

Figure 15:
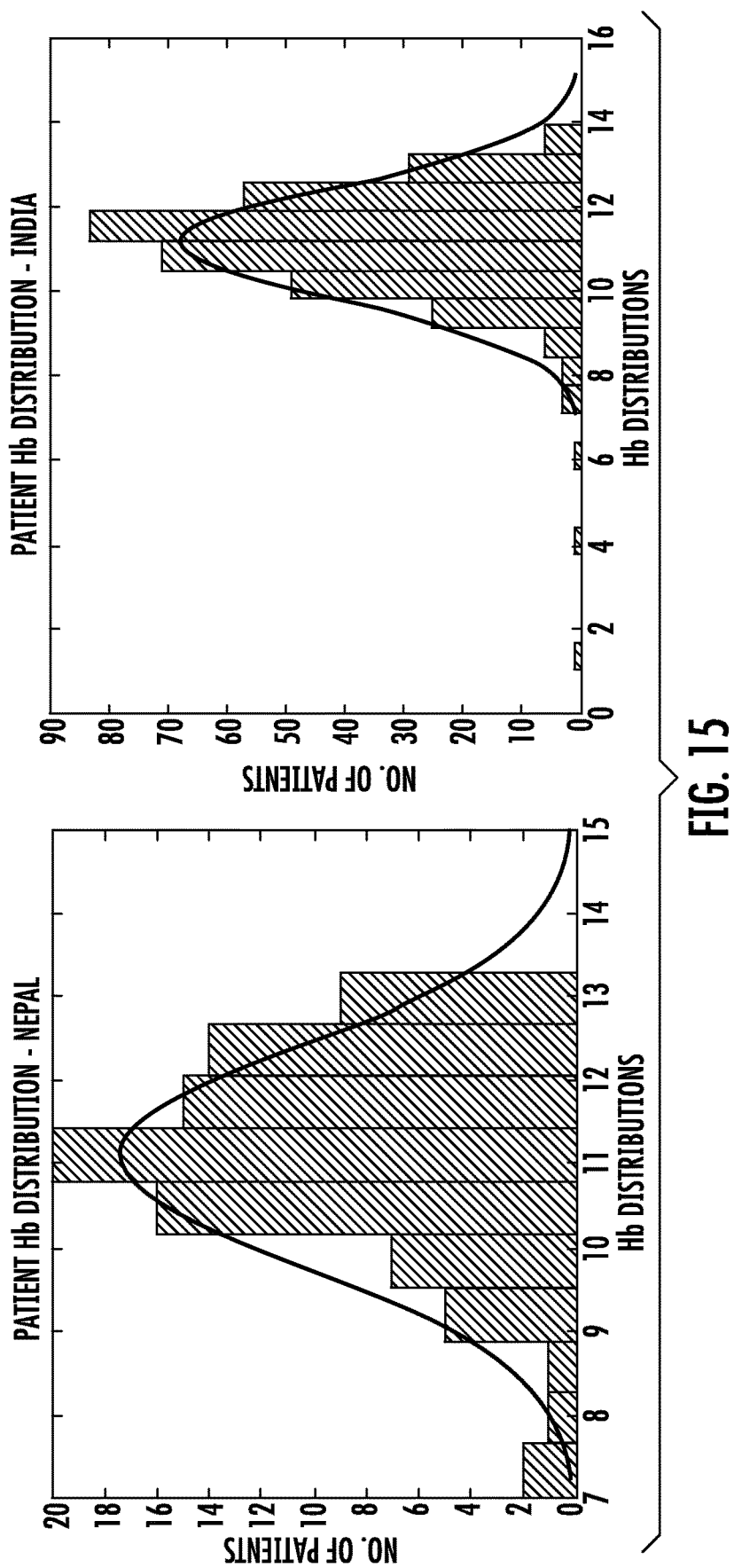
FIG. 15 illustrates a graphical view of hemoglobin distribution from the Nepal and India study sights.

Data from 120 patients was collected. Over the course of five days, patients underwent a clinically appropriate blood draw, as indicated by doctors at the anemia clinic, and participated in the use of the prototype. A set of two-wavelength probes were used to collect PPG signals from the index finger of each patient's right hand. Patient age, skin tone, and gestational age (where appropriate) were recorded during study registration when patients were assigned an identification number. Blood work was completed via an autoanalyzer in an off-site facility. Hematology data, including hemoglobin level, total blood count, and hemoglobin A1C, was compiled and de-identified by partnering clinicians, and then reported to the investigation team. The hemoglobin distribution from the gold standard blood draw from both study sites is pictured in FIG. 15. FIG. 15 illustrates a graphical view of hemoglobin distribution from the study sights.

Figure 16:
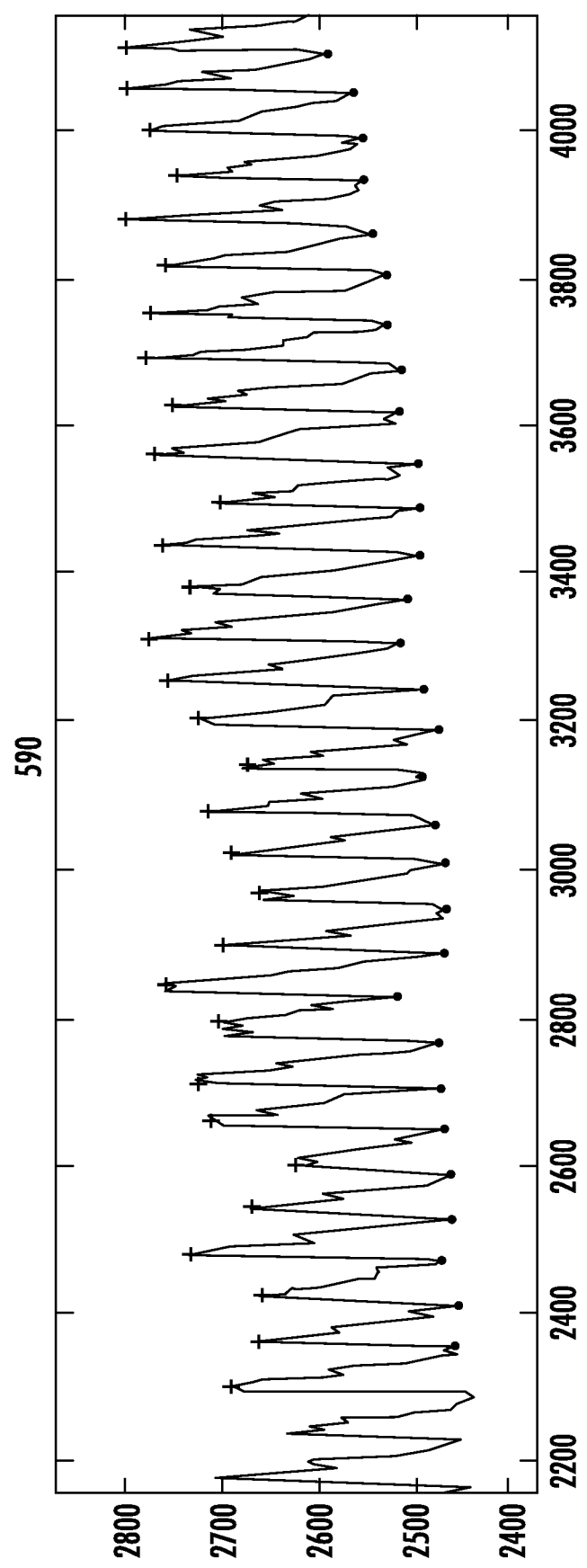
FIG. 16 illustrates a graphical view of an example of output from custom software written in MATLAB for automated feature extraction from the real-time photo-plethysmogram signal.

Data was pre-processed using a series of filters and data segments were saved where clean PPG signals could be extracted. For all usable data files, minima, maxima, ratios, and R values of each wavelength were calculated and recorded using custom Matlab software, as illustrated in FIG. 16. FIG. 16 illustrates a graphical view of an example of output from custom software written in MATLAB for automated feature extraction from the real-time photo-plethysmogram signal. Pre-processing data to extract maxima and minima for each wavelength so ratios and R values can be calculated (590 nm shown here). Red dots indicate maxima, green dots indicate minima. A median filter with tunable parameters was used to suppress motion artifacts. After processing, 104 and 182 files were left from the Nepal and India studies, respectively. 167 of the original 453 data files were unusable due to a variety of reasons including movement artifact during data collection, muted signals caused by misplacement of the finger clip, and weak signals from the lowest wavelengths which have difficulty transmitting through the finger.

Figure 17:
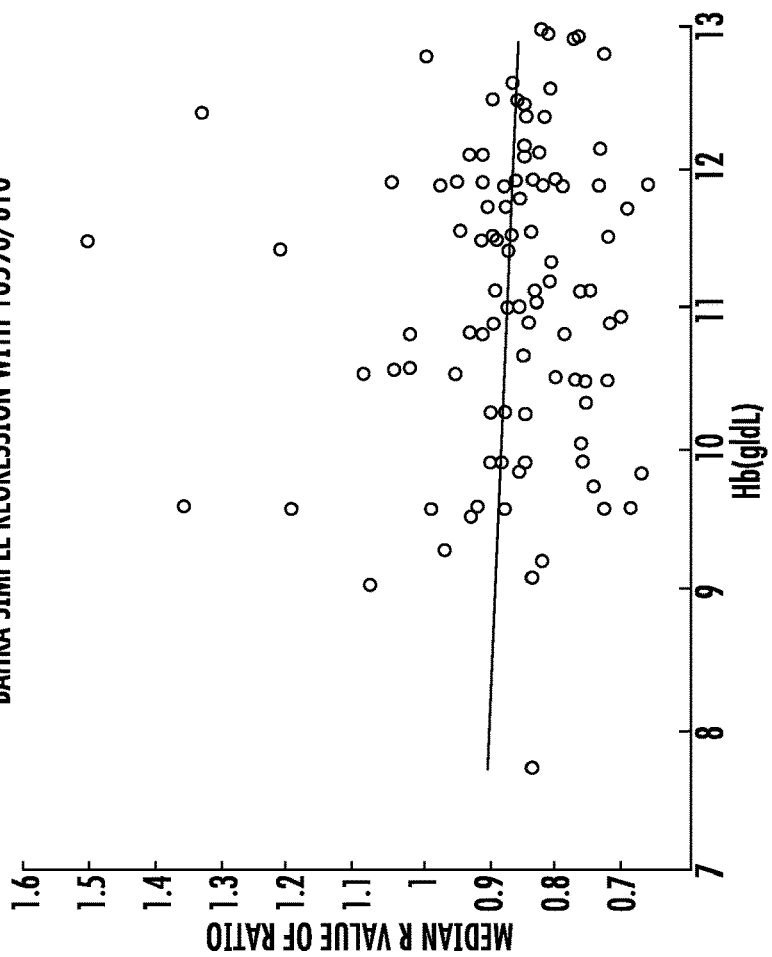
FIGS. 17-18 illustrate graphical views of the linear regression was unable to adequately predict hemoglobin.
Figure 18:
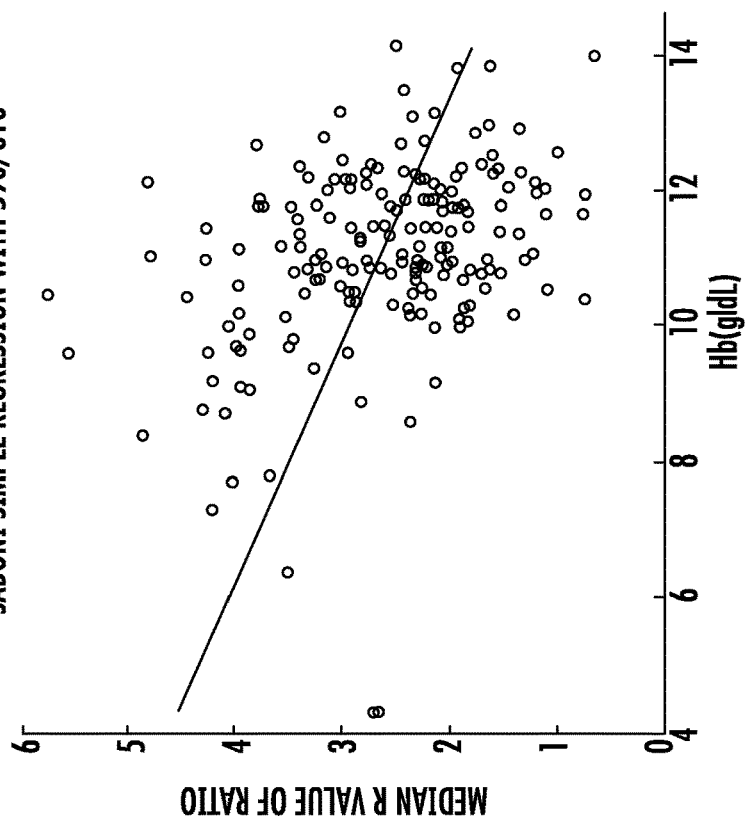

The remaining 286 patient data set was large enough to begin efforts to find a calibration curve. The first trial ran on the data was an 80:20 training using linear regression with the r values collected. This means that a random 80% of the data was chosen to in an attempt to calibrate a linear model of hemoglobin prediction using these r values. This was attempted with each of the 2-LED finger clips and various combinations of wavelengths obtained by combining data from different finger clips. The same trials were performed with data from each of the sites. As the sample results in FIGS. 17-18 illustrate graphical views of the linear regression was unable to adequately predict hemoglobin. FIGS. 17 and 18 illustrate graphical views of output from 80:20 training in a data set with r values from 590 and 810 nm (FIG. 17) and 1050 and 810 (FIG. 18)

Figure 19:
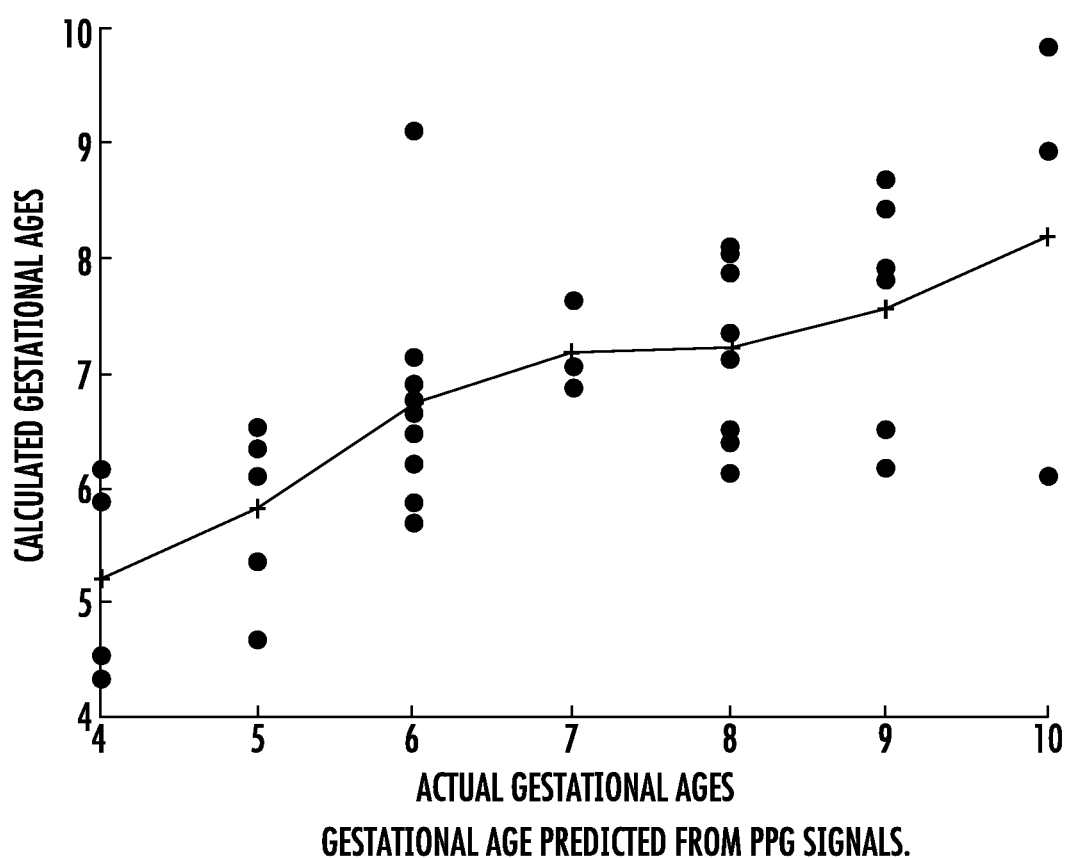
FIG. 19 illustrates gestational age predicted from PPG signals.

This data set was also used to investigate the effects of other potential confounding variables. While skin tone and device bias did not have an effect on the calibration, it appeared that the calibration was strongly dependent on gestational age. The gestational age of the patients was predictable from their PPG signals as shown in FIG. 19. FIG. 19 illustrates gestational age predicted from PPG signals. For this reason, gestational age was included as a variable in all calibration efforts moving forward.

Next, more rigorous pre-processing was done in attempt to deal with the low volume of patients in the moderate to severe anemia range gathered during the two field studies. For this reason, the input space of hemoglobin values was separated at hemoglobin values of 10 g/dL and the 80:20 training trial was repeated. This was done to examine whether the low hemoglobin values behaved differently in the regression equation than the high hemoglobin values. The results show that the regression could identify such differences in hemoglobin values with relatively high correlation coefficients.

The improved R2 from this data separation indicates that there was likely a difference in the behavior of the plethysmogram of patients with lower hemoglobin values compared to the behavior of patients with higher hemoglobin values. In order to take advantage of this non-linearity in the input-space, more rigorous machine learning algorithms were used on the data. Three different approaches were tried—Viz-Single neuron perceptron; Multi layer Feedforward Neural Networks, and Support Vector Machines (SVMs), with linear basis functions as well as radial basis functions (rbfs). The best results were obtained with rbf SVMs, and are reported here in the tables below.

| LED Set (nm) | Mean $R^2$ | S.D. |
| --- | --- | --- |
| 590/810 | 0.85 | 0.15 |
| 810/1070 | 0.87 | 0.19 |
| 940/660 | 0.75 | 0.29 |

| | Sensitivity | Specificity |
| --- | --- | --- |
| Anemic vs. Healthy | 83% | 91% |
| Mild vs. Moderate/Severe | 80% | 71% |

An SVM is a non-probabilistic binary linear classifier. This means that it is able to separate data into two discrete groups. In addition, SVMs are immune to the "curse of dimensionality" allowing it to perform well despite the scarcity of data retrieved from anemic patients. In the case of this study's data, SVM's were used in an attempt to classify anemia based on the r values output from the fingerclips. The first SVM was used to classify patients as "anemic" or "healthy" based on whether a value greater than or less than 10 was detected. After this, the patients in the anemic group were isolated and a second SVM was used to try to classify "mild" anemia as patients with hemoglobin values between 9-10 g/dL and "moderate to severe" anemia as patients below 9 g/dL. The table below shows the sensitivity and specificity of this non-linear, hierarchical classification. It is important to note that the output from the SVM's, known as "support vectors," is a matrix of constants that is usable by a mobile phone. As noted in the histograms of anemia distribution previously, there were not sufficient patients with Severe anemia, and therefore, owing to the limitations of the machine learning algorithm, had to club together two categories—Moderate+Severe. It should also be noted that these thresholds can be fine-tuned to different levels depending on the needs of the local public health program (i.e. the levels of the thresholds are changeable, but the initial calibration step would require sufficient patients in each bucket—to 'train' the device algorithm).

Figure 20:
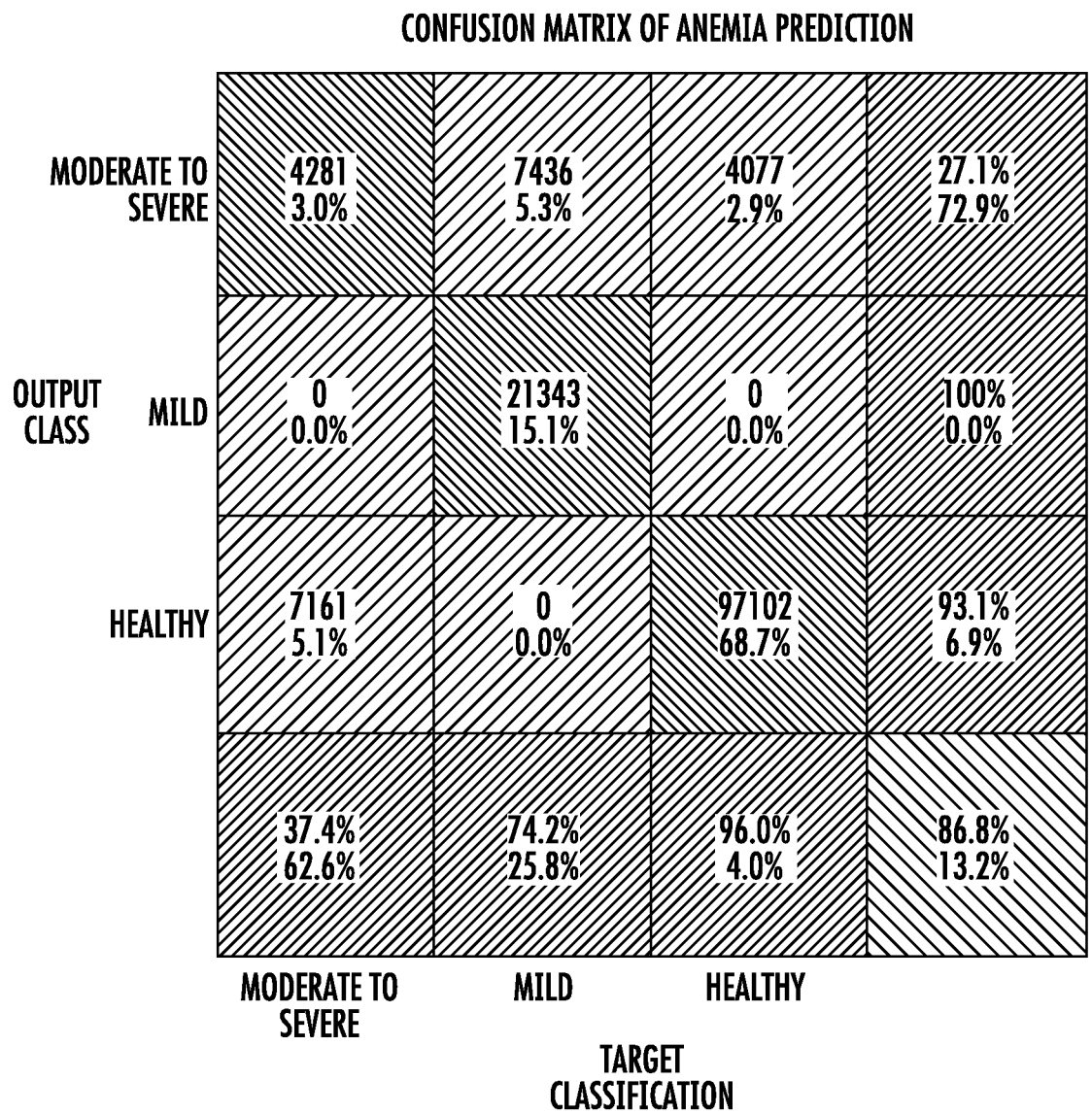
FIG. 20 illustrates a matrix view of the performance of SVM-based algorithm for patients in each category of the hierarchical anemia classification.

A confusion matrix was generated to clearly identify the strengths and weaknesses of the machine learning algorithms used. A confusion matrix shows the percentage of correct predictions and also shows the exact types of errors that the algorithm is making in each region of anemia classification (FIG. 20). FIG. 20 illustrates a matrix view of the performance of SVM-based algorithm for patients in each category of the hierarchical anemia classification. For instance, if a patient's blood draw reports that the patient is in the "healthy range" and the algorithm also outputs that the patient is in this range, the value in the green square at the intersection of the third column from the left (the "healthy" column) and the third row from the top (the "healthy" row) is increased by one. On the other hand, if the algorithm had reported that the same patient was "moderate to severely" anemic, the value in the red square at the intersection of the 3rd column from the left (the "healthy" column) and the first row (the "moderate to severe" row) is increased by one. The bottom grey row and rightmost grey column report the cumulative statistics of each row and column, while the blue square at the bottom right corner reports overall cumulative statistics.

As FIG. 20 illustrates, the algorithm performs very well for patients in the mild and healthy ranges but has relatively poor performance in the moderate to severe range. This result is likely a function of the distribution of patients that were used to train the algorithms. In other words, because of the low number of moderate to severe anemic data points obtained, the algorithm could not be trained well in this range resulting in this poor performance. This is the main reason the team would continue to attempt to collect more data in the field from patients with low hemoglobin levels.

Figure 21:
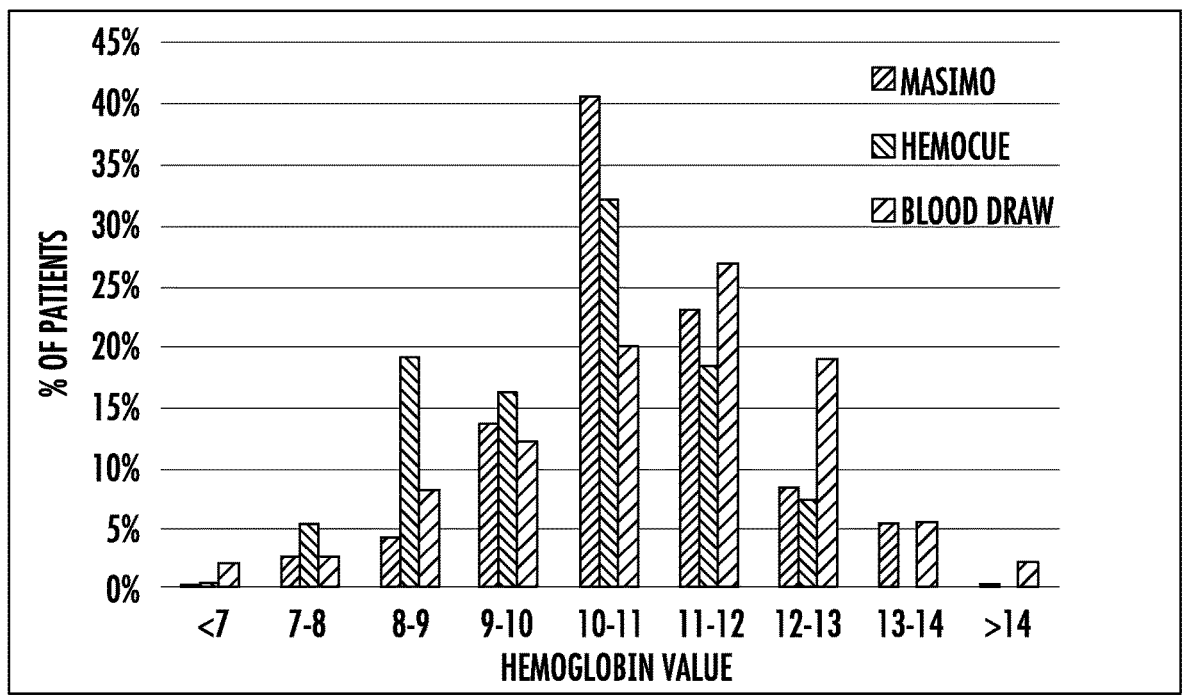
FIG. 21 illustrates a graphical view of the patient assessment according to each method.

In a second study, the team collected data from 176 patients over a five-day period. The patient set mainly included pregnant women who came in for their antenatal visits at the antenatal clinic in the hospital. The hemoglobin status of study participants was assessed with the device of the present invention, the autoanalyzer (gold standard), the HemoCue device, and the Massimo device. FIG. 21 illustrates a graphical view of the patient assessment according to each method.

The HemoCue and Masimo devices underestimate the hemoglobin number compared to the blood draw (shown below).

|  | Masimo | Blood Draw | HemoCue |
| --- | --- | --- | --- |
| # Screened | 246 | 178 | 146 |
| Mean (g/dL) | 10.80 | 10.98 | 10.16 |
| Std. Dev. | 1.32 | 1.66 | 1.39 |
| Avg. Bias (g/dL) | −0.11 | n/a | −1.01 |

The team collected plethysmographic data using six different two LED, common 810 nm, computer-based finger clip sensors. A total of 12 PPGs were collected from each patient, out of which 6 were obtained from 810 nm. In order to process the data recovered from the finger clips, preprocessing steps were taken to ensure the fidelity of the output of the clips. First, the data was passed through a band-pass filter and the "clean" peaks were identified. Then, the ratio of Vmax:Vmin was taken for the clean peaks at each wavelength and this value was reported as the "r" value. The r value used for each patient in the regression equations was the median of the r values from each patient's plethysmogram.

$r\lambda = Vmax/Vmin$

SVMs were used in an attempt to classify anemia based on the r values output from the finger clips. The average of all r810 was used as the scaled value for r for 810 nm. All other wavelengths were appropriately scaled to normalize the data across all finger clips. The reported data analysis used the 590 nm, 660 nm, 810 nm, and 940 nm wavelengths as input parameters. Similar simulations were run with other combinations, but this combination outperformed the others. Although, substituting the 590 nm for the 569 nm wavelength generates similar accuracy results. Wavelengths were included as independent variables, while the hemoglobin level from the gold standard autoanalyzer was the dependent variable. When the gestational age is used as one of the independent variables, the gestational age months was used (1-9 months).

During the second study, there weren't many patients with very low hemoglobin (below 9 gm/dL). Twenty of the 176 patients had hemoglobin below 9 gm/dL. The lower concentration of people with moderate to severe anemia affected the calculations and tended to give very low accuracy. As such, the data was resampled from different points in the PPG (about 30 seconds of PPG data was collected) for these patients. In this way, the data points were tripled from patients below with hemoglobin concentration below 9 gm/dL. The extracted features were then compared against the gold standard (autoanalyzer and cyanomethemoglobin methods) to obtain a correlation. The table below shows accuracy results reported from the second study data. These results show that SVMs with radial basis functions, can categorize patients into three buckets (based on the three thresholds). Ideally the last bucket would be below 7 g/dL or lower, but owing to the very limited number of patients recorded below those numbers, analysis was limited to proving the viability of the 'three bucket' categorization (i.e. normal, mildly anemic, moderately/severely anemic). Based on these results, the next study is targeting ongoing anemia camps in more rural areas where greater anemia prevalence data was expected to be recorded.

| Hemoglobin Threshold | Sensitivity | Specificity |
| --- | --- | --- |
| 9.0 g/dL | 0.767 | 0.894 |
| 10.0 g/dL | 0.763 | 0.864 |
| 11.0 g/dL | 0.694 | 0.767 |

At both 11.0 gm/dL and 10.0 gm/dL, high sensitivity and specificity are obtained, allowing us to potentially set the bucket thresholds at these specific hemoglobin points (Table 10). This supports the hypothesis that the device is useful as a screening tool because 10.0 g/dL can be used as the cutoff between healthy and anemic and 9.0 g/dL as the cutoff between mild and moderate/severe anemia.

The statistical analysis indicated that the hemodynamics for pregnant women at late stages of gestation are different than those at earlier gestational ages. This was attributed to factors such as increased water retention. The team re-ran the second study statistical analysis to include gestational age in the input space as an independent variable. However, this time a significant increase or decrease in accuracy was not seen, in the table below. The table shows accuracy results reported from the second study data with gestational age included as an independent variable. In this study, unlike in the third study data, no significant differences in using Gestational age as an additional input variable to the classification algorithm were seen.

| Hemoglobin Threshold | Sensitivity | Specificity |
| --- | --- | --- |
| 9.0 g/dL | 0.750 | 0.867 |
| 10.0 g/dL | 0.761 | 0.857 |
| 11.0 g/dL | 0.689 | 0.714 |

Another algorithm was introduced (which albeit more computationally complex, can be used on a phone platform, or through cloud computing methods). Known as ensemble assignment, the technique uses an ensemble (or committee of) independently trained classifiers to predict an outcome by taking a vote among committee members to estimate the final predicted value. Increasing the number of classifiers, or committee members, in an ensemble can help increase the sensitivity and specificity of classification. Ensembles consisting of 3, 11, and 51 committee members, were experimented with as shown in the table below. The table shows accuracy of the device when using an ensemble assignment data analysis technique with differing number of committee members. Note that the overall accuracy of the Four Category classification (around the three thresholds) goes up based on the number of ensemble members. Individual members were trained independently and can have slightly different internal structure. Note that the three thresholds selected are a limitation of the data collected in the study, and could likely by re-assigned to lower values in future validation studies.

| Hemoglobin Threshold | 3 member committee | | 11 member committee | | 51 member committee | |
|---|---|---|---|---|---|---|
| | Sens. | Spec. | Sens. | Spec. | Sens. | Spec. |
| 9.0 g/dL | 0.720 | 0.875 | 0.783 | 0.897 | 0.762 | 0.905 |
| 10.0 g/dL | 0.726 | 0.875 | 0.745 | 0.875 | 0.731 | 0.872 |
| 11.0 g/dL | 0.677 | 0.811 | 0.706 | 0.815 | 0.712 | 0.795 |

The 11 member committee member outperformed both the 3 and 51 member committee. The team will continue to experiment with ensemble assignment as the patient data set is bolstered and the algorithm development refined. One potential downside of the technique is the amount of computing power necessary to run a simulation. Cloud computing would be required in order to make this technique feasible. Because of the potential to improve the accuracy, the team is intrigued by this approach and cloud computing is discussed in the Continued Development section.

In a fourth study, the team collected data from 345 patients over a 3 day field study. All the finger clip sensors and control instrumentation of the present invention used in the field lasted the duration of the data collection effort (>300 uses each). Again, a gold standard autoanalyzer was used as a reference for PPG signals collected with the devices. The data is currently being analyzed to draw conclusions on the device's algorithm.

Figure 22:
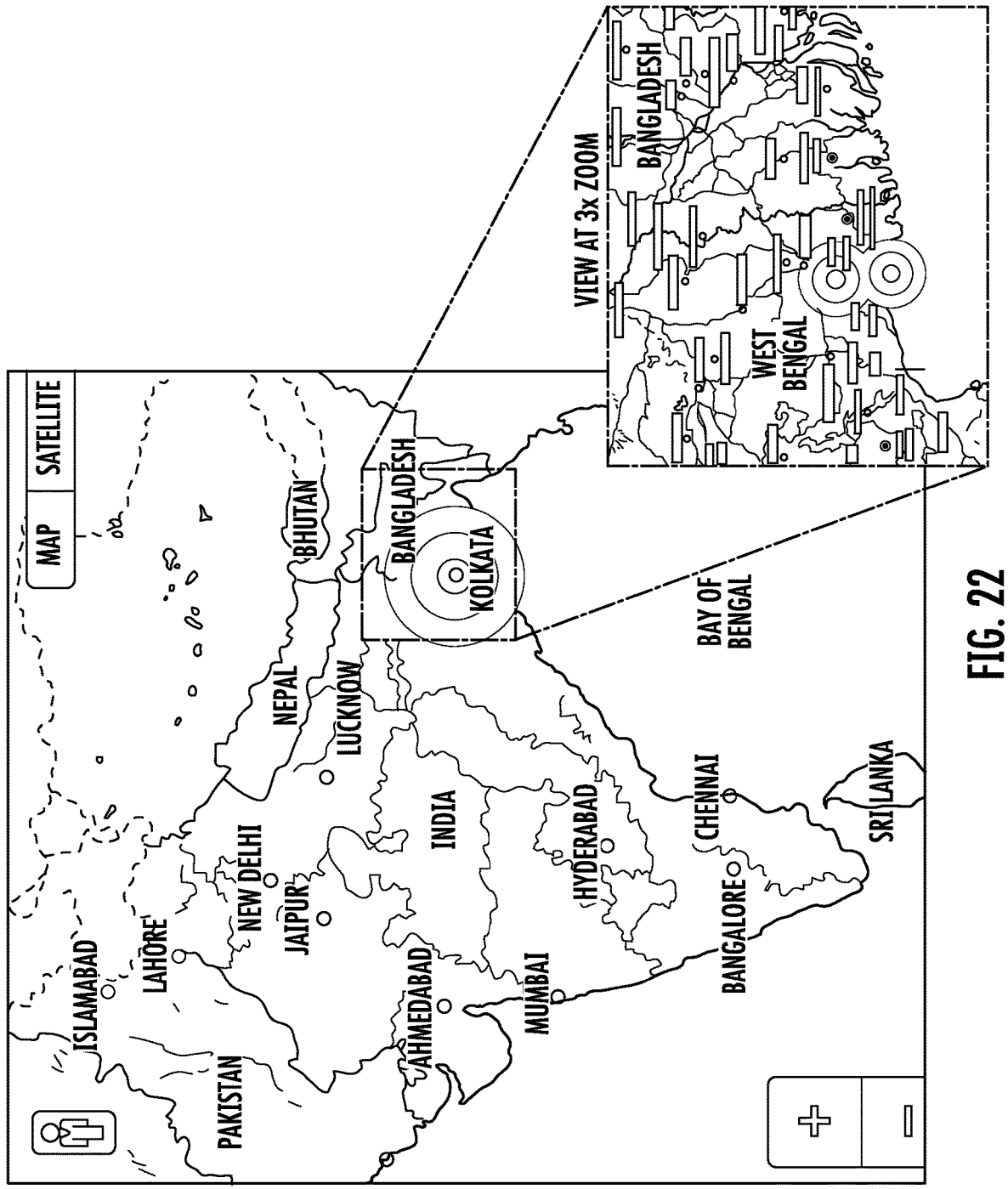
FIG. 22 illustrates real-time mapping of anemia prevalence data to the cloud during the July field study. The telemedicine enabled aspect of the device represents a shift in thinking towards the possibility of more effective resource allocation programs.

FIG. 22 is a screenshot from the fourth study. FIG. 22 illustrates real-time mapping of anemia prevalence data to the cloud during the July field study. The telemedicine enabled aspect of the device represents a shift in thinking towards the possibility of more effective resource allocation programs. As sensors are added to the platform, in-country health administrators could see similar maps to make governmental healthcare decisions across a number of patient disease states (anemia, hypertension, pre-eclampsia, etc). Interestingly, there was no internet available in the village clinics, so the device worked as expected by storing data until an internet connection was established, then offloading all patient data to the cloud. Names were replaced by patient ID numbers to de-identify all patient data. The heat map shown demonstrates the screen that would be seen by Ministries of Health at the state or national level. As the device gets used across the country, the heat map would adjust, showing the geographic areas most in need. Resource allocation decisions could be made based on this information. Compared to the current standard of care, which compiles data every 5 years, this system operates in real-time.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A system comprising:
a mobile communication device; and
a sensor system comprising:
a plurality of light emitting diodes (LEDs) configured to transmit light through tissue of a subject at four wavelengths;
a photosensor configured to receive and measure the light transmitted through the tissue of the subject by the plurality of LEDs; and
a communications board configured to:
modulate a series of switches that alternate power distribution to each of four transmitting channels,
supply, using a pulse width modulator, self-adjusting current levels to the plurality of LEDs,
trigger the plurality of LEDs in accordance with the alternating power distribution and the self-adjusting current levels to transmit the light through the tissue of the subject,
receive information related to the light transmitted through the tissue of the subject and received by the photosensor, and
communicate with the mobile communication device.

2. The sensor system of claim 1, further comprising:
an LED driver.

3. The sensor system of claim 2, further comprising:
a timer coupled to the LED driver.

4. The system of claim 1, further comprising:
a power source for providing power to the sensor system.

5. The system of claim 4, wherein the power source comprises:
one or more of the mobile communication device or a battery.

6. The system of claim 1, wherein the communications board comprises:
an amplifier.

7. The system of claim 6, wherein the amplifier is one of an amplitude modulation (AM) device or a binary frequency shift keying (BFSK) device.

8. The system of claim 1, wherein the mobile communication device comprises:
a cellular telephone.

9. The system of claim 1, wherein the mobile communication device comprises:
a headset-in jack, and
a headset-out jack.

10. The system of claim 1, wherein the plurality of LEDs comprise five LEDs.

11. The system of claim 10, wherein the four wavelengths are four distinct wavelengths selected from 522, 569, 570, 590, 660, 810, 940, 1050, or 1070 nm.

12. The system of claim 1, wherein a device of the system is configured to:
analyze the information using multiple classifiers.

13. The system of claim 1, wherein a device of the system is configured to:

classify, using a support vector machine, a patient as normal, mild anemia, moderate anemia, or severe anemia.

14. The system of claim 1, wherein the plurality of LEDs are further configured for cycling through a plurality of wavelengths.

15. The system of claim 14, wherein the plurality of LEDs are further configured for applying each of the plurality of wavelengths for 20 ms.

16. The system of claim 1, wherein the system is further configured to:
analyze data received from the communications board using a non-linear classification algorithm.

17. The system of claim 16, wherein the non-linear classification algorithm is applied using one of Support Vector Machines or Neural Networks.

18. The system of claim 1, further comprising:
a graphical user interface for input of data and display of results.

19. A method, comprising:
modulating, by a device, a series of switches that alternate power distribution to each of four transmitting channels;
supplying, by the device and using a pulse width modulator, current levels to a plurality of light emitting diodes (LEDs);
triggering, by the device, the plurality of LEDs in accordance with the alternating power distribution and the current levels to transmit light through tissue of a subject;
transmitting, by the device and based on triggering the plurality of LEDs, the light through the tissue of the subject at four wavelengths;
receiving, by the device and via a photosensor, the light transmitted through the tissue of the subject; and
communicating, by the device and to a mobile communication device, information related to the light transmitted through the tissue of the subject and received via the photosensor.

20. The method of claim 19, further comprising:
amplifying the light transmitted through the tissue of the subject and received via the photosensor; and
wherein communicating the information comprises:
communicating the information based on amplifying the light transmitted through the tissue of the subject and received via the photosensor.

* * * * *